United States Patent [19]

Sih

[11] 4,109,082

[45] Aug. 22, 1978

[54] TRANS,TRANS-2,3,4,5-TETRADEHYDRO-PGI$_1$, COMPOUNDS

[75] Inventor: John C. Sih, Kalamazoo, Mich.

[73] Assignee: The Upjohn Company, Kalamazoo, Mich.

[21] Appl. No.: 821,541

[22] Filed: Aug. 3, 1977

[51] Int. Cl.$^2$ ............................................. C07D 307/93
[52] U.S. Cl. .................................. 542/426; 542/416; 542/418; 542/421; 542/429; 260/346.22; 260/346.73
[58] Field of Search ...................... 260/346.22, 346.73; 542/421, 429, 426, 416, 418

[56] References Cited

PUBLICATIONS

Johnson et al., Prostaglandins 12, 915 (1976).

*Primary Examiner*—Henry R. Jiles
*Assistant Examiner*—Bernard Dentz
*Attorney, Agent, or Firm*—Robert A. Armitage

[57] ABSTRACT

This invention relates to certain structural and pharmacological analogs of prostacyclin (PGI$_2$) wherein the C-5 to C-6 double bond is isomerized to the C-4 to C-5 position. These novel trans-4,5-didehydro-5,6-dihydro prostacyclin-type compounds are useful as smooth muscle stimulators.

42 Claims, No Drawings

TRANS,TRANS-2,3,4,5-TETRADEHYDRO-PGI$_1$, COMPOUNDS

BACKGROUND OF THE INVENTION

This invention relates to novel structural and pharmacological analogs of prostacyclin (PGI$_2$). In particular, the present invention relates to prostacyclin-type compounds wherein the C-5 to C-6 double bond of prostacyclin is isomerized to the C-4 to C-5 position.

Prostacyclin is an endogenously produced compound in mammalian species, being structurally and biosynthetically related to the prostaglandins (PG's ). In particular, prostacyclin exhibits the following structure and atom numbering:

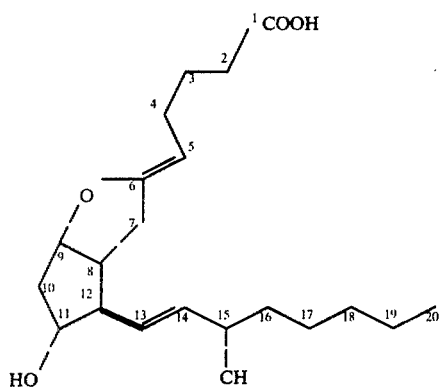

5,6-Dihydroprostacyclin exhibits the following structure and atom numbering:

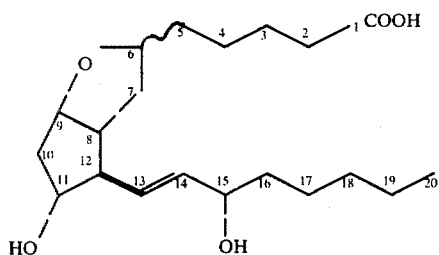

As is apparent from inspection of formulas I and II, prostacyclin and 5,6-dihydroprostacyclin (i.e., PGI$_1$) bear a structural relationship to PGF$_2\alpha$, which exhibits the following structure and atom numbering:

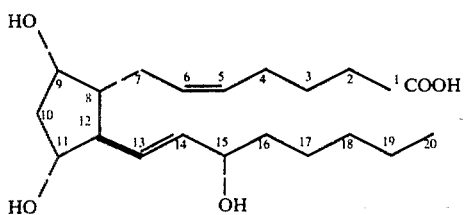

As is apparent by reference to formula III, prostacyclin and 5,6-dihydroprostacyclin may be trivially named as a derivative of PGF-type compounds. Accordingly, prostacyclin is trivially named 9-deoxy-6,9α-epoxy-(5Z)-5,6-didehydro-PGF$_1$ and 5,6-dihydro prostacyclin is named 9-deoxy-6,9α-epoxy-PGF$_1$. For description of the geometric stereoisomerism employed above, see Blackwood et al., Journal of the American Chemical Society 90, 509 (1968). Further, for a description of prostacyclin and its structural identification, see Johnson et al., Prostaglandins 12, 915 (1976).

For convenience, the novel prostacyclin analogs described herein will be referred to by the trivial, artrecognized system of nomenclature described by N. A. Nelson, Journal of Medicinal Chemistry, 17, 911 (1974) for the prostaglandins. Accordingly, all of the novel prostacyclin derivatives herein will be named as 9-deoxy-PGF$_1$-type compounds or alternatively and preferably as PGI$_1$ or PGI$_2$ derivatives.

In the formulas above, as well as in formulas hereinafter, broken line attachments to any ring indicate substituents in "alpha" (α) configuration i.e., below the plane of such ring. Heavy solid line attachments to any ring indicate substituents in "beta" (β) configuration, i.e., above the plane of such ring. The use of wavy lines (~) herein will represent attachment of substituents in either the alpha or beta configuration or attachment in a mixture of alpha and beta configurations.

The side-chain hydroxy at C-15 in the above formulas is in S or R configuration, as determined by the Cahn-Ingold-Prelog sequence rules. See J. Chem. Ed. 41:16 (1964). See also Nature 212, 38 (1966) for discussion of the stereochemistry of the prostaglandins, which discussion applies to the novel prostacyclin analogs herein. Further, the carboxy-terminated side chain is attached to the heterocyclic ring of PGI in either the alpha or beta configuration, which by the above convention represents the (6R) or (6S) configuration, respectively. Expressions such as C-4, C-5, C-6, C-15, and the like, refer to the carbon atom in the prostaglandin or prostacyclin analog which is in the position corresponding to the position of the same number in PGF$_2\alpha$ or prostacyclin, as enumerated above.

Molecules of PGI$_1$, PGI$_2$, and the novel, asymmetric prostacyclin analogs each have several centers of asymmetry, and can exist in racemic (optically inactive) form and in either of the two enantiomeric (optically active) forms, i.e., the dextrorotatory and levorotatory forms. As drawn, the above formula for PGI$_2$ corresponds to that endogenously produced in mammalian tissues. In particlar, refer to the stereoconfiguration at C-8 (alpha), C-9 (alpha), C-11 (alpha), and C-12 (beta) of endogenouslyproduced prostacyclin. The mirror image of the above formula for prostacyclin represents the other enantiomer. The racemic forms of prostacyclin contains equal numbers of both enantiomeric molecules, and the above formula I and its mirror image is needed to represent correctly the corresponding racemic prostacyclin.

For convenience hereinafter, use of the term prostaglandin ("PG") or prostacyclin ("PGI$_2$") will mean the optically active form of that prostaglandin or prostacyclin thereby referred to with the same absolute configuration as PGF$_2\alpha$, obtained from mammalian tissues.

The term "prostaglandin-type" or "prostacyclin-type" (PG-type or PGI-type) product, as used herein, refers to any monocyclic or bicyclic cyclopentane derivative herein which is useful for at least one of the same pharmacological purposes as the prostaglandins or prostacyclin, respectively.

The formulas as drawn herein, which depict a prostaglandin-type or prostacyclin-type product or an intermediate useful in their respective preparations, each represent the particular steroisomer of the prostaglandin-type or prostacyclin-type product which is of the same relative stereochemical configuration as a corresponding prostaglandin or prostacyclin obtained from mammalian tissues, or the particular stereoisomer of the intermediate which is useful in preparing the above stereoisomer of the prostaglandin-type or prostacyclin-type products.

The term "prostacyclin analog", as used herein, represents that stereoisomer of a prostacyclin-type product which is of the same relative stereochemical configuration as prostacyclin obtained from mammalian tissues or a mixture comprising that stereoisomer and the enantiomer thereof. In particular, where a formula is used to depict a prostacyclin-type product herein, the term "prostacyclin analog" refers to the compound of that formula or a mixture comprising that compound and the enantiomer thereof.

Subsequent to any invention disclosed herein trans-4,5-didehydro-PGI$_1$ was reported by Nicolaou, et al., J. C. S. Chem. Comm. 1977:331–332 and Corey, et al., JACS 99:2006–2008 (1977).

SUMMARY OF THE INVENTION

The present specification particular discloses:
I. a prostacyclin analog of the formula

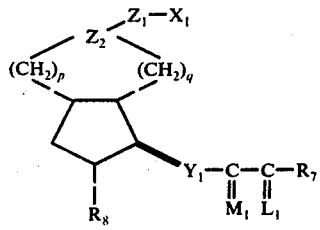

IV wherein $Z_2$ is

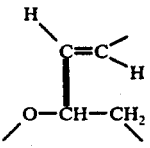  (1)

or

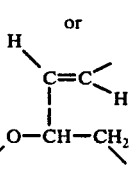  (2)

wherein one $p$ and $q$ is the integer zero or one and the other is the integer zero;
wherein $Z_1$ is
(1) —(CH$_2$)$_g$—CH$_2$—CH$_2$—, or
(2) —(CH$_2$)$_g$—CH$_2$—CF$_2$—,
wherein $g$ is the integer zero, one, or 2;
wherein $R_8$ is hydrogen, hydroxy, or hydroxymethyl;
wherein $Y_1$ is
(1) trans—CH=CH—,
(2) cis—CH=CH—, or
(3) —CH$_2$CH$_2$—,
wherein $M_1$ is

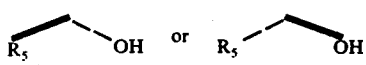

wherein $R_5$ is hydrogen or alkyl with one to 4 carbon atoms, inclusive, wherein $L_1$ is

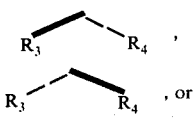

a mixture of

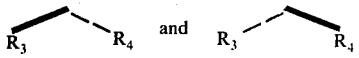

wherein $R_3$ and $R_4$ are hydrogen, methyl, or fluoro, being the same or different, with the proviso that one of $R_3$ and $R_4$ is fluoro only when the other is hydrogen or fluoro;
wherein $X_1$ is
(1) —COOR$_1$ wherein R$_1$ is hydrogen; alkyl of one to 12 carbon atoms, inclusive; cycloalkyl of 3 to 10 carbon atoms, inclusive; aralkyl of 7 to 12 carbon atoms, inclusive phenyl; phenyl substituted with one, two or three chloro or alkyl of one to 3 carbon atoms; phenyl substituted in the para position by

 (a)

 (b)

 (c)

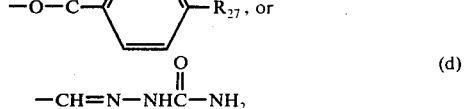 (d)

wherein R$_{25}$ is methyl, phenyl, acetamidophenyl, benzamidophenyl, or —NH$_2$; R$_{26}$ is methyl, phenyl, —NH$_2$, or methoxy; and R$_{27}$ is hydrogen or acetamido; inclusive, phenacyl, i.e.,

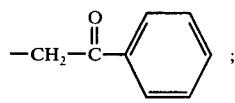 ;

phenacyl substituted in the para position by chloro, bromo, phenyl, or benzamido; or a pharmacologically acceptable cation;
(2) —CH$_2$OH;
(3) —CH$_2$NL$_2$L$_3$ wherein L$_2$ and L$_3$ are hydrogen or alkyl of one to 4 carbon atoms, inclusive; or
(4) —COL$_4$, wherein L$_4$ is
(a) Amino of the formula —NR$_{21}$R$_{22}$; wherein R$_{21}$ and R$_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl phenyl substituted with one, 2, or 3 chloro, alkyl of one to 3 carbon atoms, inclusive, hydroxy, carboxy, alkoxycarbonyl of one to 4 carbon atoms, inclusive, or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro; pyridyl; pyridyl substituted by one, 2, or 3 chloro, alkyl of one to 3 carbon atoms, inclusive, or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms inclusive, hydroxy, or alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of $R_{21}$ and $R_{22}$ is other than hydrogen or alkyl;

(b) cycloamino selected from the group consisting of

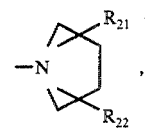 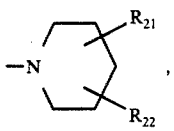

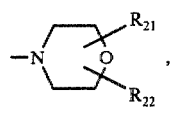 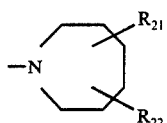

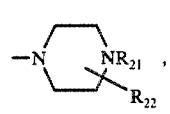 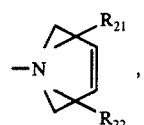

or

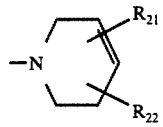

wherein $R_{21}$ and $R_{22}$ are as defined above;

(c) carbonylamino of the formula $-NR_{23}COR_{21}$, wherein $R_{23}$ is hydrogen or alkyl of one to 4 carbon atoms and $R_{21}$ is as defined above;

(d) sulphonylamino of the formula $-NR_{23}SO_2R_{21}$, wherein $R_{21}$ and $R_{22}$ are as defined above; or (e) hydrazino of the formula $-NR_{23}R_{24}$, wherein $R_{23}$ is as defined above and $R_{24}$ is amino of the formula $-NR_{21}R_{22}$. as defined above, or cycloamino, as defined above;

wherein $R_7$ is (1) $-(CH_2)_m-CH_3$,

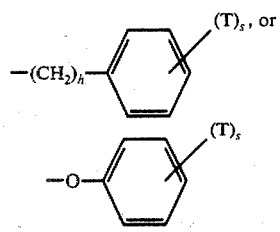

wherein $m$ is the integer one to 5, inclusive, $h$ is the integer zero to 3, inclusive; $s$ is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl; and the pharmacologically acceptable acid addition salts thereof when $X_1$ is $-CH_2NL_2L_3$.

II. a prostacyclin analog of the formula

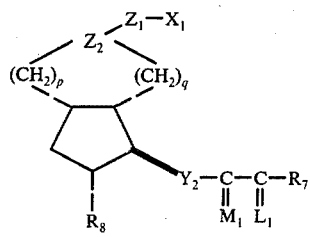

wherein $X_1$, $Z_1$, $Z_2$, $p$, $q$, $R_8$, $M_1$, $L_1$, and $R_7$ are as defined above; and wherein $Y_2$ is $-C\equiv C-$, and the pharmacologically acceptable acid addition salts thereof when $X_1$ is $-CH_2CH_{NL2}L_3$.

III. a prostacyclin analog of the formula

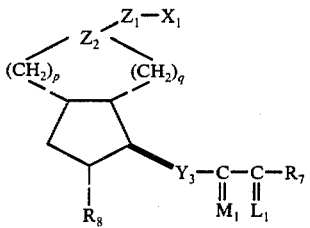

wherein $X_1$, $Z_2$, $p$, $q$, $R_8$, $M_1$, $L_1$, and $R_7$ are as defined above;

wherein $Z_3$ is trans—CH=CH—, wherein $Y_3$ is (1) trans—CH=CH—, (2) cis—CH=CH—, (3) —CH$_2$CH$_2$—, or (4) —C≡C— and the pharmacologically acceptable acid addition salts thereof when $X_1$ is $-CH_2NL_2L_3$.

For the novel compounds herein wherein $Z_1$ is $-(CH_2)_g-CH_2-CF_2-$, such compounds are referred to herein as 2,2-difluoro-PG-type compounds. Further, compounds herein wherein $Z_3$ is trans —CH=CH— are named as trans-2,3-didehydro-PG-type compounds.

When $q$ is zero and $g$ is one or 2, the compounds described herein are additionally named as 2a-homo-PG-type or 2a,2b-dihomo-PG-type compounds, respectively. In this event the additional methylene or ethylene group is considered for the purposes of nomenclature as though it were inserted between the carbon atoms C-2 and C-3. Further, such additional carbon atoms are denoted as C-2a and C-2b, counting from the C-2 to the C-3 carbon atoms, respectively.

When $q$ is one and $g$ is zero, one, or 2, the novel compounds herein are further designated as 7a-homo-PG-type, 2a,7a-dihomo- or 2a,2b,7a-trihomo-PG-type compounds respectively. In the former case, a methylene group between C-7 and the cyclopentane ring is considered to have been inserted, thereby resulting in the attachment of this ring to C-7a. In the latter cases, the rationale for the nomenclature is as described above for compounds wherein $g$ is one or two.

Moreover, when $p$ is one the compounds herein are referred to as 9-deoxy-6,9α-epoxymethylene-PGF$_1$-type compounds.

The novel prostacyclin analogs herein wherein $R_8$ is hydrogen or hydroxymethyl are respectively referred to as 11-deoxy-PG-type or 11-deoxy-11-hydroxymethyl-PG-type compounds. Additionally, when $Y_1$, $Y_2$, or $Y_3$ is cis—CH=CH—, —CH$_2$CH$_2$—, or —C≡C—, the novel compounds thereby referred to are named as 13-cis-PG-type, 13,14-dihydro-PG-type, or 13,14-didehydro-PG-type compounds, respectively.

Compounds herein wherein $M_1$ is

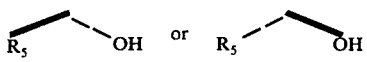

and $R_5$ is alkyl are referred to as 15-alkyl-PG-type compounds.

With the exception of the 13-cis-PG-type compounds described above, all the above compounds exhibiting a hydroxy or alkoxy moiety in the beta configuration at C-15 are additionally referred to as 15-epi-PG-type compounds. For the 13-cis-PG-type compounds herein, only compounds exhibiting the hydroxy of alkoxy moiety in the alpha configuration at C-15 are referred to as 15-epi-PG-type compounds. The rationale for this system of nomenclature with respect to the natural and epimeric configurations at C-15 is described in U.S. Pat. No. 4,016,184, issued Apr. 5, 1977.

When $R_7$ is —(CH$_2$)$_m$—CH$_3$ wherein $m$ is as defined above, the novel compounds herein are named as 19,20-dinor-PG-type, 20-nor-PG-type, 20-methyl-PG-type or 20-ethyl-PG-type compounds when $m$ is one, 2, 4, or 5, respectively When $R_7$ is

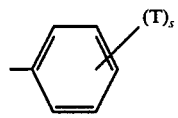

wherein T and $s$ are as defined above, and neither $R_3$ nor $R_4$ is methyl, the novel compounds herein are named as 16-phenyl-17,18,19,20-tetranor-PG-type compounds, when $s$ is zero. When $s$ is one, 2, or 3, the corresponding compounds are named as 16-(substituted phenyl)-17,18,19,20-tetrnor-PG-type compounds. When one and only one of $R_3$ and $R_4$ is methyl or both $R_3$ and $R_4$ are methyl, then the corresponding compounds wherein $R_7$ is as defined in this paragraph are named as 16-phenyl- or 16-(substituted phenyl)-18,19,20-trinor-PG-type; or 16-methyl-16-phenyl- or 16-methyl- or 16-(substituted phenyl)-18,19,20-trinor-PG-type compounds, respectively.

When $R_7$ is

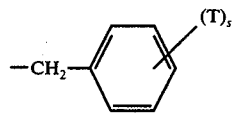

wherein T and $s$ are as defined above, the novel compounds herein are named as 17-phenyl-18,19,20-trinor-PG-type compounds, when $s$ is 0. When $s$ is one, 2, or 3, the corresponding compounds are named as 17-(substituted phenyl)-18,19,20-trinor-PG-type compounds.

When $R_7$ is

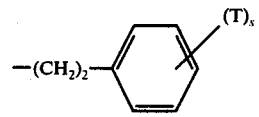

wherein T and $s$ are as defined above, the novel compounds herein are named as 18-phenyl-19,20-dinor-PG-type compounds, when $s$ is 0. When $s$ is one, 2, or 3, the corresponding compounds are named as 18-(substituted phenyl)-19,20-dinor-PG-type compounds.

When $R_7$ is

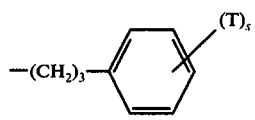

wherein T and $s$ are as defined above, the novel compounds herein are named as 19-phenyl-20-nor-PG-type compounds, when $s$ is 0. When $s$ is one, 2, or 3, the corresponding compounds are named as 19-(substituted phenyl)-20-nor-PG-type compounds.

When $R_7$ is wherein T and $s$ are as defined above, and neither $R_3$ nor $R_4$ is methyl, the novel compounds herein are named as 16-phenoxy-17,18,19,20-tetranor-PG-type compounds, when $s$ is zero. When $s$ is one, 2, or 3, the corresponding compounds are named as 16-(substituted phenoxy)-17,18,19,20-tetranor-PG-type compounds. When one and only one of $R_3$ and $R_4$ is methyl or both $R_3$ and $R_4$ are methyl, then the corresponding compounds wherein $R_7$ is as defined in this paragraph are named as 16-phenoxy- or 16-(substituted phenoxy)-18,19,20-trinor-PG-type compounds or 16-methyl-16-phenoxy- or 16-substituted phenoxy)-18,19,20-trinor-PG-type compounds, respectively.

When at least one of $R_3$ and $R_4$ is not hydrogen then (except for the 16-phenoxy or 16-phenyl compounds discussed above), there are thusly described the 16-methyl-PG-type (one and only one of $R_3$ and $R_4$ is methyl), 16,16-dimethyl-PG-type ($R_3$ and $R_4$ are both methyl), 16-fluoro-PG-type (one and only one of $R_3$ and $R_4$ is fluoro), and 16,16-difluoro-PG-type ($R_3$ and $R_4$ are both fluoro) compounds For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is —CH$_2$OH, —CH$_2$NL$_2$L$_3$, or tetrazolyl, the novel compounds herein are named respectively as 2-decarboxy-2-hydroxymethyl-PG-type compounds, 2-decarboxy-2-aminomethyl-PG-type compounds, or 2-decarboxy-2-tetrazolyl-PG-type compounds.

Then $X_1$ is —COL$_4$ the novel compounds herein are named as PG-type, amides. Further when $X_1$ is —COOR$_1$, the novel compounds herein are named as PG-type, esters and PG-type, salts when $R_1$ is not hydrogen.

Finally, the NOMENCLATURE TABLE herein describes the convention by which trivial names are further assigned for the novel compounds herein;

NOMENCLATURE TABLE

| $Z_2$ | p | q | Compound type |
|---|---|---|---|
| (1) | 0 | 0 | (6S)-9-deoxy-6,9α-epoxy-trans-4,5-didehydro-PGF$_1$-type compounds |
| $\begin{array}{c} H \\ \diagdown \\ C{=}C \\ \vert \quad \diagdown H \\ \vert \\ O{-}CH{-}CH_2 \\ \diagup \quad \diagdown \end{array}$ | 0 | 1 | (6S)-7a-homo-9-deoxy-6,9α-epoxy-trans-4,5-didehydro-PGF$_1$-type compounds |
|  | 1 | 0 | (6S)-9-deoxy-6,9α-epoxymethylene-trans-4,5-didehydro-PGF$_1$-type compounds |
| (2) | 0 | 0 | (6R)-9-deoxy-6,9α-epoxy-trans-4,5-didehydro-PGF$_1$-type compounds |
| $\begin{array}{c} H \\ \diagdown \quad \quad C \\ C{=}C \quad \diagup \\ \vert \quad \diagdown H \\ \vert \\ O{-}CH{-}CH_2 \\ \diagup \quad \diagdown \end{array}$ | 0 | 1 | (6R)-7a-homo-9-deoxy-6,9α-epoxy-trans,4,5-didehydro-PGF$_1$-type compounds |
|  | 0 | 1 | (6R)-9-deoxy-6,9α-epoxymethylene-trans-4,5-didehydro-PGF$_1$-type compounds |

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inculsive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tylyl, p-ethylphenyl, p-tert-butylphenyl, 2,5-dimethylphenyl, 4-chloro-2-methylphenyl, and 2,4-dichloro-3-methylphenyl.

Examples of

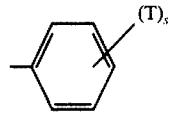

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-trimethylphenyl, (o-, m-, p-)fluorophenyl, 2-fluoro-(o, m-, or p-)tolyl, 4-fluoro-2,5-xylyl, (2,4-, 2,5-, 2,6-3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-, m-, or p-trifluoromethylphenyl, (o-, m-, or p-methoxyphenyl, (o-, m-, or p-)ethoxyphenyl, (4- or 5-)chloro-2-methoxyphenyl, and 2,4-dichloro(5- or 6-)methylphenyl.

Examples of phenyl esters substituted in the para position (i.e. $X_1$ is $-COOR_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel prostacyclin amides herein (i.e. $X_1$ is $COL_4$) include the following:

(1) Amides within the scope of alkylamino groups of the formula $-NR_{21}R_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Amides within the scope of aralkylamino are benzylamide, 2-phenylethylamide, 2-phenylethylamide, N-methyl-N-benzylamide, and dibenzylamide. Amides within the scope of substituted phenylamino are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanalide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butyl-benzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pryidylamide, and γ-pryidylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylaklylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamino are 4-methyl-α-pyridylmethylamide, 4-methyl-β-pyridylmethylamide, 4-chloropyridylmethylamide, 4-chloro-β-pyridylmethylamide, 4-methyl-α-pyridylethylamide, 4-methyl-β-pyridylethylamide, 4-chloropyridylethylamide, 4-chloro-β-pyridylethylamide, 4-methyl-α-pyridylpropylamide, 4-methyl-β-pyridylpropylamide, 4-chloro-pyridylpropylamide, 4-chloro-β-pyridylpropylamide, 4-methyl-β-pyridylbutylamide, 4-methyl-α-pyridylbutylamide, 4-chloropyridylbutylamide, 4-chloro-β-pyridylbutylamide, 4-methyl-β-pyridylbutylamide. Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)-propylamide, and α,α-dimethyl-β-hydroxyethylamide. Amides within the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxyethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula $-NR_{23}COR_{21}$ are methylcarbonylamide, ethylcarbonylamide, phenylcarbonylamide, and benzylcarbonylamide. Amides within the scope of sulfonylamino of the formula $-NR_{23}SO_2R_{21}$ are methylsulfonylamide, ethylsulfonylamide, phenylsulfonylamide, p-tolylsulfonylamide, benzylsulfonylamide.

(4) Hydrazides within the scope of the above hydrazino groups are hydrazine, N-aminopiperidine, benzoylhydrazine, phenylhydrazine, N-aminomorpholine, 2-hydroxyethylhydrazine, methylhydrazine, 2,2,2-hydroxyethylhydrazine and p-carboxyphenylhydrazine.

The term "pharmacologically acceptable acid addition salt" refers to those known acid addition salts of amine-containing compounds which are relatively nontoxic and readily acceptable to the host animal. Especially preferred are those acid addition salts which facilitate pharmaceutical formulation (e.g., more readily crystalline, etc.) or are readily and easily available for use. In particular, examples of acids from which such salts may be prepared are hydrochloric acid, hydrobromic acid, sulphuric acid, phosphoric acid, and other acids such as tartaric acid, fumaric acid, maleic acid, methanesulfonic acid, and p-toluene sulfonic acid.

The term "pharmacologically acceptable cation" refers to those pharmacologically acceptable salts of the prostacyclin-type carboxylic acids ($X_1$ is $-COOH$) described above which are conventionally employed with prostaglandins. In particular, such pharmacologically acceptable salts include pharmacologically acceptable metal cations, amine cations, and quarternary amonium cations. Additionally, basic amino acids such as arginine and lysine are employed. Further, certain amine cations such as THAM [tris(hydroxymethyl-)amino methyl] and adamanamine are especially useful for the present purposes. Additionally, U.S. Pat. No. 3,016,184, issued Apr. 5, 1977 (particularly column 29), describes salts which are likewise preferred for the present purposes.

The novel prostacyclin analogs disclosed herein produce smooth muscle stimulation.

Accordingly, the novel prostacyclin analogs disclosed herein are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys).

The novel prostacyclin analogs herein are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight and condition of the patient or animal.

The novel prostacyclin analogs herein are thus surprisingly and unexpectedly useful for pharmacological purposes, rendering these compounds pharmacological as well as structural analogs of prostacyclin. Moreover, the prostacyclin analogs herein exhibit a more prolonged chemical stability, facilitating their formulation and use as pharmacological agents.

Further, the novel prostacyclin analogs of the present invention where $X_1$ is —$COOR_1$ or —$COL_4$ and of the 15α-hydroxy configuration

(i.e., $M_1$ is $R_5$   OH), are useful as antithrombotic, antiulcer, antiasthma, and antidermatosis agents, as indicated below:

(a) Platelet Aggregation Inhibition.

These novel prostaglandin analogs are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The preferred dosage form for these compounds is oral, although other non-parenteral routes (e.g., buccal, rectal, sublingual) are likewise employed in preference to parenteral routes. Oral dosage forms are conventionally formulated (tablets, capsules, et cetera) and administered 2 to 4 times daily. Doses in the range of about 0.05 to 100 mg./kg. of body weight per day are effective.

The addition of these compounds to whole blood provides in vitro applications such as, storage of whole blood to be used in heart-lung machines. Additionally whole blood containing these compounds can be circulated through organs, e.g. heart and kidneys, which have been removed from a donor prior to transplant. They are also useful in preparing platelet rich concentrates for use in treating thrombocytopenia, chemotherapy, and radiation therapy. In vitro applications utilize a dose of 0.001-1.0 µg/ml of whole blood.

(b) Gastric Secretion Reduction.

These novel prostacyclin analogs are also useful in mammals, including man and certain useful animals, e.g., dogs and pigs, to reduce and control gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. to about 20 µg. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Preferably, however, the novel prostacyclin analogs are administered orally or by other nonparenteral routes. As employed orally, one to 6 administrations daily in a dosage range of about 1.0 to 100 mg./kg. of body weight per day is employed. Once healing of the ulcers has been accomplished the maintenance dosage required to prevent recurrence is adjusted downward so long as the patient or animal remains asymptomatic.

(c) NOSAC-Induced Lesion Inhibition. These novel prostacyclin analogs herein are also useful in reducing the undesirable gastrointestinal effects resulting from systemic administration of anti-inflammatory prostaglandin synthetase inhibitors, and are used for that purpose by concomitant administration of the prostaglandin derivative and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins. Accordingly these novel prostacyclin analogs herein are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

(d) Bronchodilation. (Antiasthma) These novel prostacyclin analogs are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostacyclin analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

(e) Dermatosis Reversal.

These novel prostacyclin analogs are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratotis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably, but incompletely cleared, or completely cleared.

For these purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients; constitute from about 0.1% to about 15% by weight of the composition, preferably from about 0.5% to about 2%. In addition to topical administration, injection may be employed, as intradermally, intra- or peri-lesionally, or subcutaneously, using appropriate sterial saline compositions.

Within the scope of the novel prostacyclin analogs described above, certain compounds are preferred in that they exhibit increased potency, selectivity of action, or otherwise represent especially convenient and useful agents.

Accordingly, preferred compounds are those wherein $p$ and $q$ are the integer zero. Further, with respect to $Z_1$, preferred compounds are those wherein $Z_1$ is $-(CH_2)_g-CH_2-CH_2-$. Further, $g$ is preferably the integer zero or 2, most preferably being zero. With respect to the $Y_1$ moiety, preferred compounds are those wherein $Y_1$ is trans—$CH=CH-$ or $-CH_2CH_2-$, the most especially preferred compounds being those wherein $Y_1$ is trans—$CH=CH-$. With respect to the $M_1$ moiety, preferred compounds are those wherein $M_1$ is

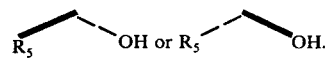

$R_5$ is preferably hydrogen, methyl, or ethyl, most preferably being hydrogen or methyl.

With respect to the $L_1$ moiety, those compounds wherein $R_3$ and $R_4$ are the same are preferred. Further preferred are those compounds herein wherein at least one of $R_3$, $R_4$, and $R_5$ is hydrogen. In the event $Y_1$, $Y_2$, or $Y_3$ is cis—$CH=CH-$ or $-C\equiv C-$, compounds wherein $R_3$, $R_4$, and $R_5$ are all hydrogen are preferred.

With respect to the integers $m$, $h$, and $s$, it is preferred that $m$ be the integer 3, $h$ be the integer zero or one and $s$ be the integer zero or one. Further, T is preferably chloro, fluoro, or trifluoromethyl.

Further preferred are the carboxylic acids or derivatives, i.e., esters, especially the p-substituted phenyl esters, and amides. With respect to the novel amides herein, preferred compounds are those wherein $R_{21}$ and $R_{22}$ are preferably hydrogen or alkyl of one to 8 carbon atoms, inclusive, being the same or different, preferably with the total number of carbon atoms in $R_{21}$ and $R_{22}$ being less than or equal to 8. More especially preferred are those amides wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to 4. Further, $R_{23}$ is preferably hydrogen.

The charts herein describe the method by which the novel prostacyclin analogs herein are prepared from known or readily synthesized starting materials.

With respect to these charts, $p$, $q$, $L_1$, $M_1$, $X_1$, $X_2$, $X_3$, $Y_1$, $Y_3$, $Z_1$, $Z_2$, $Z_3$, $R_1$, $R_7$, and $R_8$ are as defined above.

$R_{36}$ is $-OR_{10}$, $-CH_2OR_{10}$, or hydrogen, wherein $R_{10}$ is a readily acid hydrolyzable blocking group such as tetrahydrofuranyl or tetrahydropyranyl. For examples of blocking groups especially contemplated by the present invention see U.S. Pat. No. 4,016,184, issued Apr. 5, 1977. $R_{38}$ is $-OSi(G_1)_3$, $-CH_2OSi(G_1)_3$, or hydrogen, where $-Si(G_1)_3$ are silyl groups, particularly those described in U.S. Pat. No. 4,016,184.

Further, $X_2$ is $-COOR_{11}$, $-CH_2OR_{10}$, or $-COL_4$, wherein $R_{11}$ is an ester within the scope of $R_1$, wherein $R_1$ is defined above and $R_{10}$ and $L_4$ are as defined above. $M_6$ is

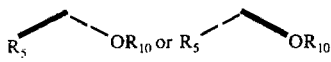

and $M_7$ is

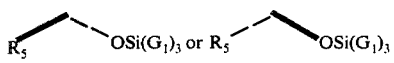

wherein $R_5$, $-Si(G_1)_3$, and $R_{10}$ are as defined above.

$Y_4$ is trans$-CH=C(Hal)$, wherein Hal is chloro, bromo, or iodo. Ac is acetyl and SePh is phenylselenyl.

$X_3$ is $-COOR_{11}$, $-CH_2OH$, $-COL_4$, wherein $R_{11}$ and $L_4$ are as defined above.

With respect to Chart A a method is provided whereby the formula XXI PGF$_2\alpha$ ($q$ is zero) or cis-4,5-didehydro-PGF$_2\alpha$ ($q$ is one) compound is transformed to the novel prostacyclin analogs of formula XXIII.

The various formula XXI compounds employed as starting materials in the present synthesis are conveniently prepared from known or readily available starting materials. Formula XXI encompasses compounds deoxygenated at C-11 (11-deoxy-PG-type compounds) or substituted at C-11 by an hydroxymethyl in place of the hydroxy (11-deoxy-11-hydroxymethyl-PG-type compounds). These compounds are prepared by methods known in the art from corresponding PGA$_2$- or cis-4,5-didehydro PGA$_1$-type compounds. Such PGA$_2$- or cis-4,5-didehydro-PGA$_1$-type compounds are conveniently prepared by acid dehydration of the corresponding PGE$_2$- or cis-4,5-didehydro-PGE$_1$-type compounds referred to above. Thus, all of the various compounds within the scope of formula XXI represent either known prostaglandin analogs or can be readily prepared by employment of conventional chemical reactions on known prostaglandin type starting materials.

By a variation of the procedure of Chart A, the formula XXI PGF$_2\alpha$ or cis-4,5-didehydro-PGF$_1\alpha$ compounds depicted therein are in mono- or bis-etherated form, whereby the respective hydroxyls, except for the C-9 hydroxy are transformed to corresponding ether derivatives. Ether groups are selected from those $R_{10}$ blocking groups known to be successfully and conventionally employed in this synthesis of prostaglandin type products from various intermediates, being readily hydrolyzable from the formula XXIII product under acid conditions. Most particularly, tetrahydrofuranyl is a convenient and readily available moiety employed for such purposes.

CHART A

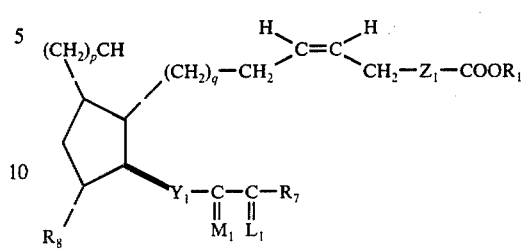

XXI

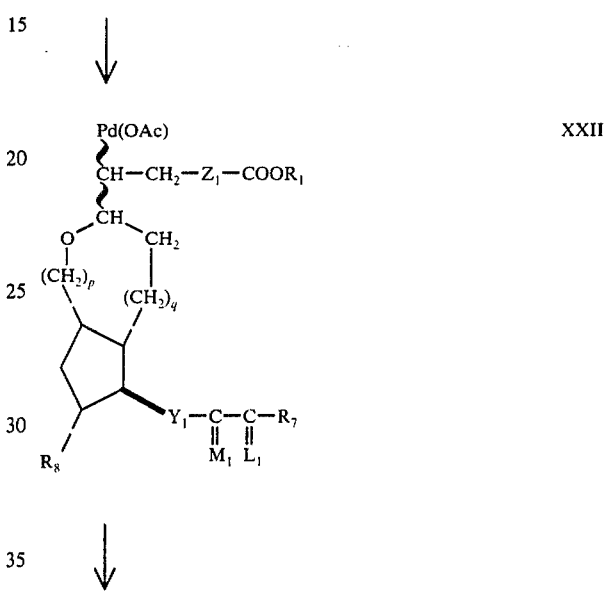

XXII

XXIII

CHART B

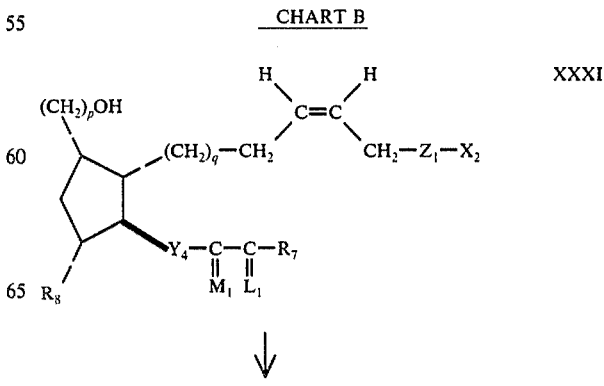

XXXI

-continued
CHART B
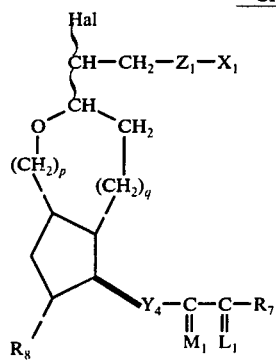
XXXII
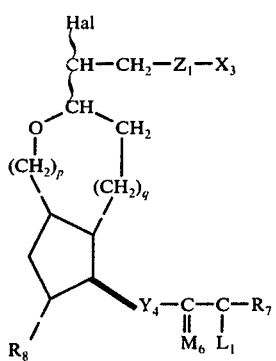
XXXIII
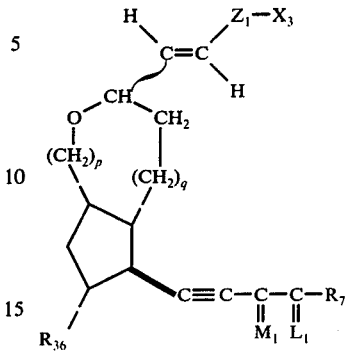
XXXIV
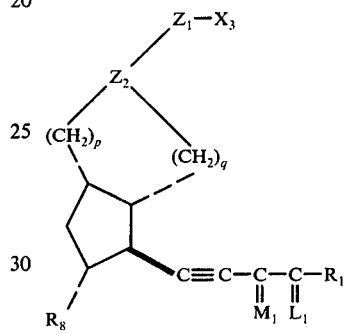
XXXV
CHART C
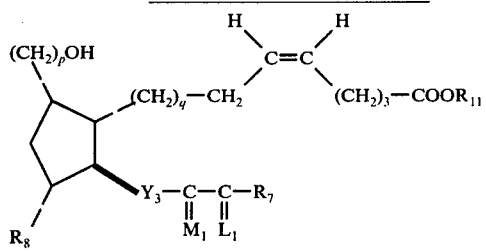
XLI
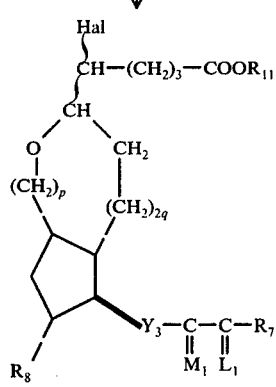
XLII

-continued
CHART C
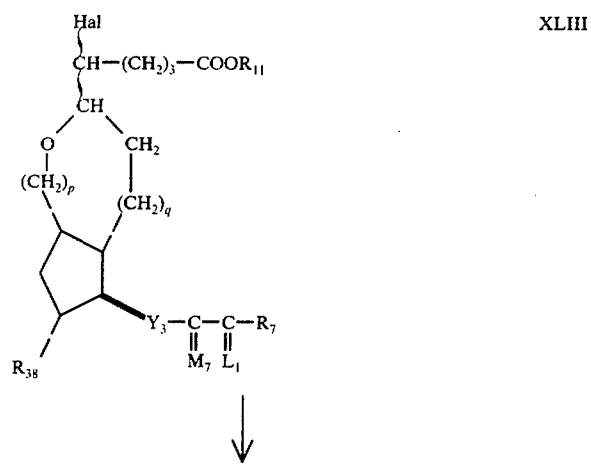
XLIII
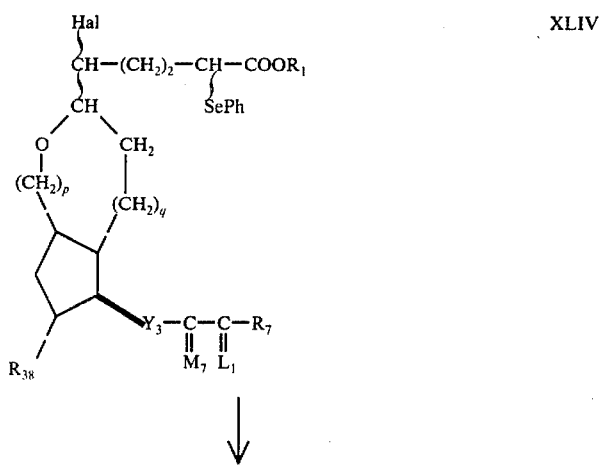
XLIV
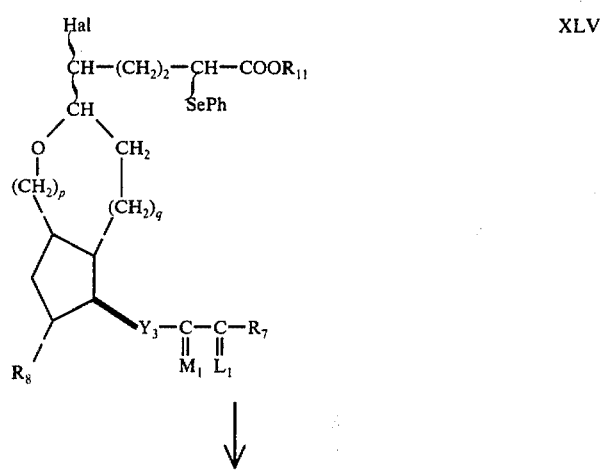
XLV

-continued
CHART C
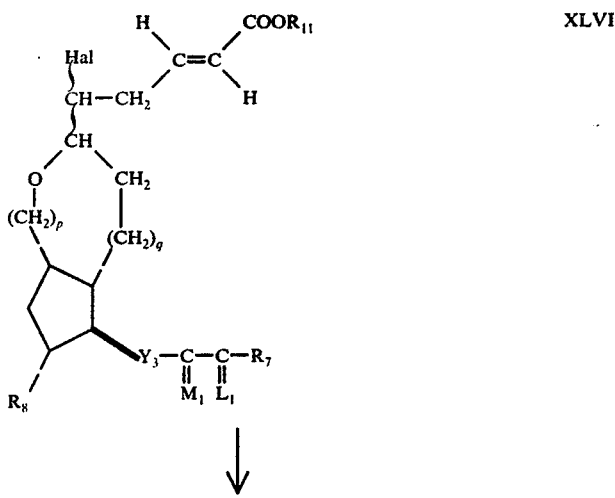
XLVI
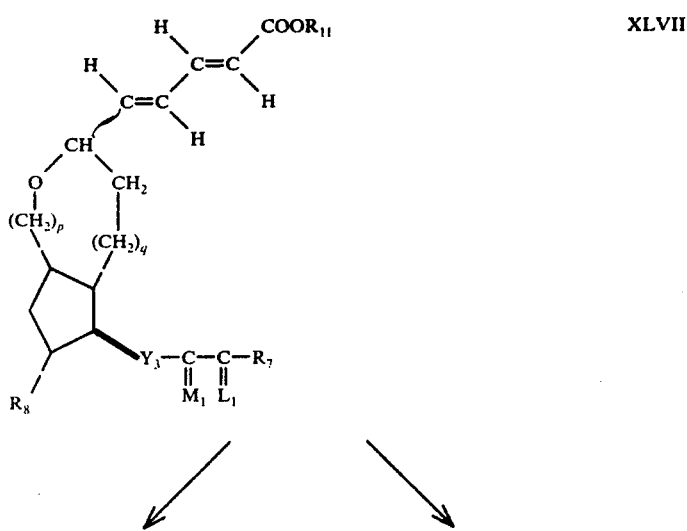
XLVII
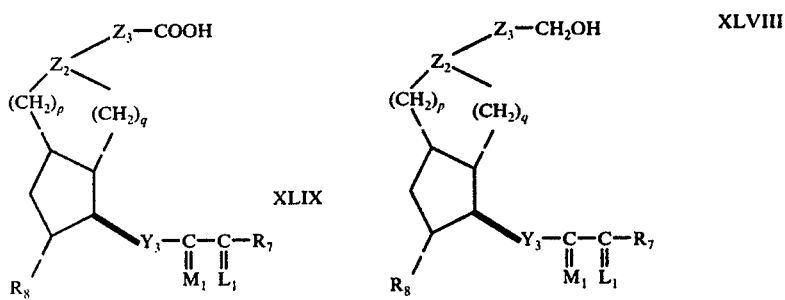
XLVIII
XLIX

CHART C -continued

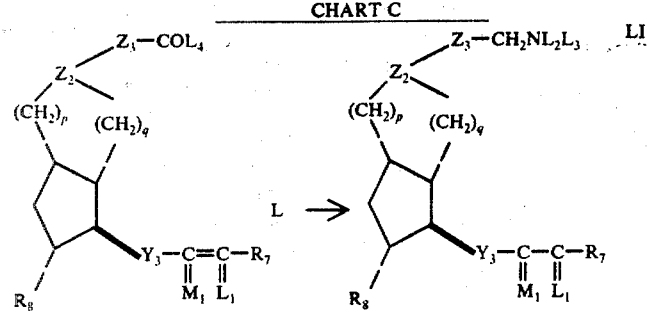

CHART D

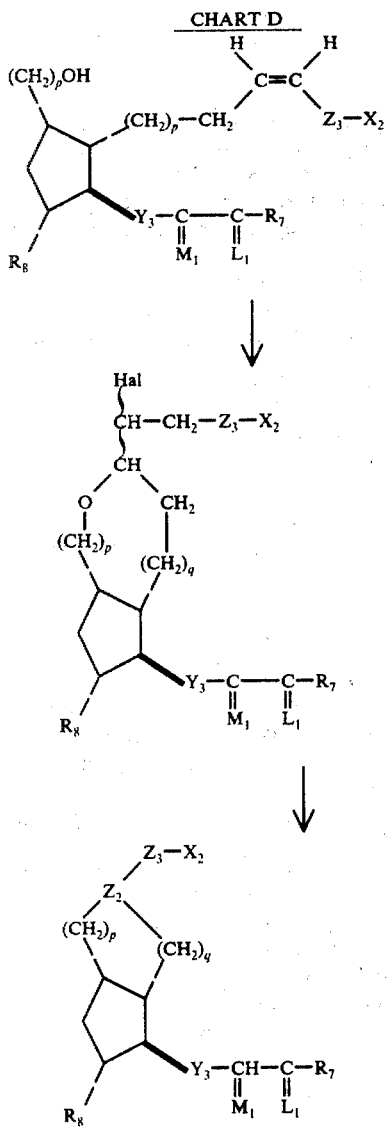

With respect to Chart A, the formula XXI PGF$_2$α- or 9-deoxy-9α-hydroxymethyl PGF$_2$-type compounds is transformed to the formula XXIII prostacyclin analogs herein by acetylpalladiocyclization, yielding the formula XXII bicyclic intermediate, followed by elimination, yielding the formula XXIII product.

With respect to this two step procedure outlined above, preferred reaction solvents are lower alkanol, particularly methanol but including, for example, isopropanol and tert-butanol. Further, the cyclization-/elimination is ordinarily complete within several hours, the reaction being run for convenience at 0°–50° C.

The two step cyclization/elimination described above is also undertaken by the procedure described in Nicolaou, et al. J.C.S. Chem. Communications 1977: 331–332, wherein a phenylselenocyclization is followed by elimination in anhydrous potassium carbonate and methanol, yields the formula XXIII product.

By an optional and preferred procedure according to Chart A, the formula XXI or formula XXII 11,15-bis(ethers) according to $R_{10}$ are employed in place of the free hydroxy compounds therein, yielding on elimination an etherified formula XXIII product. By this optional and preferred procedure, the $R_{10}$ ethers are thereafter hydrolyzed under mild acetic conditions (tetrahydrofuran in aqueous acetic acid), yielding the formula XXIII product.

The etherified compounds corresponding to formula XXI are obtained by methods known in the art or are themselves known in the art and the etherified compounds corresponding to formula XXII are prepared by methods known in the art. See the references referred to above with respect to such $R_{10}$ ethers.

Chart B provides a method whereby the formula XXXI PGF$_2$α-type compound is transformed to the various formula XXXV 4,5,13,14-tetradehydro-PGI$_1$-type products of the present invention.

The formula XXXII compound of Chart B is prepared from the formula XXXI compound by halocyclization. When Hal of the formula XXXII compound is iodo, this halocyclization proceeds by reacting the formula XXXI compound with potassium iodide or an alkali metal carbonate or bicarbonate in an organic system containing iodide. In the latter case, solvents such as methylene chloride are employed. Further, reaction temperatures at or below ambient temperature, preferably about 0° C. are employed. The reaction is then quenched by addition of sodium sulfate and sodium carbonate, yielding the formula XXXII iodo compound. When Hal is bromo, a convenient brominating agent is N-bromosuccinimide. Solvents such as methylene chloride are employed and the reaction proceeds at between 0° and ambient temperature to completion. When recovery of pure formula XXXII product is desired, chromatographic methods for its isolation in pure form are employed. High pressure liquid chromatography is an especially useful technique for this purpose.

The formula XXXIII compound is then prepared from the formula XXXII compound by transforming any free hydroxyls to their corresponding $R_{10}$ ethers. Methods provided in the reference above are employed in this transformation.

The formula XXXIV compound is then obtained from the formula XXXIII compound by a double dehydrohalogenation. By this method, the formula XXXIII 5,14-dihalo PG-type compound is transformed to the formula XXXIV 4,5,13,14-tetradehydro $PGI_1$-type compound.

For this double dehydrohalogenation, basic conditions are employed. Preferably, dehydrohalogenation proceeds in a mixture of lower alkanol and dimethyl sulfoxide as reaction solvent and potassium tert-butoxide as base. The formula XXXIV compound thusly obtained is then hydrolyzed to the formula XXXV prostacyclin analogs herein under mild acetic conditions. For example, mixtures of tetrahydrofuran and aqueous acetic acid are employed.

Chart C provides a method whereby the 2,3,4,5-tetradehydro-prostacyclin analogs of formula XLVII-LI are prepared from the formula XLI $PGF_2\alpha$-type compound.

With respect to Chart C the formula XLII compound is prepared from the formula XLI compound by halocyclization, as described in Chart B.

This formula XLII compound is then transformed to the corresponding formula XLIII silyl ether by methods known in the art. See for example the reference provided above.

The formula XLIV compound is then prepared from the formula XLIII compound by α-phenylselenization. Accordingly, in the preparation of this phenylselenyl derivative, the formula XLIII compound is first reacted with Lithio-N-isopropylcyclohexylamine, thereby generating the C-2 anion corresponding to formula XLIII. Finally, this anion is reacted with diphenylselenide, yielding a formula XLIV compound.

Thereafter, the formula XLV compound is prepared by hydrolysis of the silyl groups, employing mild acidic conditions (e.g., the mineral acid).

The formula XLV compound is then transformed to the formula XLVI compound by dehydrophenylselenization, yielding a trans-2,3-didehydro-5-halo-$PGI_1$-type intermediate.

This formula XLVI intermediate is then dehydrohalogenated to the formula XLVII compound under basic conditions, as described above. This formula XLVII ester is then saponified (e.g., potassium hydroxide in methanol), yielding the formula XLIX acid. This acid is then transformed herein by amidization to the formula L prostacyclin analogs. Further, when $L_4$ is $NH_2$, the formula L prostacyclin amides are reduced with lithium aluminum hydride to the corresponding formula LI 2-decarboxy-2-aminomethyl compound ($L_2$ and $L_3$ are hydrogen). This 2-decarboxy-2-aminomethyl compound is then transformed to corresponding secondary and tertiary amines (either one or both of $L_2$ and $L_3$ are alkyl) by methods known in the art. See for methods of preparing the various 2-decarboxy-2-aminomethyl analogs herein the procedures of U.S. Pat. No. 4,028,350.

Alternatively, the formula XLVII compound is reduced to the formula XLVIII 2-decarboxy-2-hydroxymethyl compound by methods known in the art for the transformation of prostaglandin analogs to corresponding prostanols. Accordingly, lithium aluminum hydride reduction is employed in this transformation. See U.S. Pat. No. 4,028,419 for a description of the preparation of such C-1 alcohols for certain bicyclic prostaglandin analogs.

Finally, Chart D provides an alternative method for the preparation of the 2,3,4,5-tetradehydro PGI-type compounds herein, which comprises employing a formula LXI 2,3-didehydro-$PGF_2\alpha$-type compound according to formula LXI and thereafter halocyclizing and dehydrohalogenating this compound to the formula XLIII product. In accordance with Chart D, methods described above for halocyclization and dehydrohalogenation are employed.

According to the above charts, the novel prostacyclin analogs herein are obtained first as primary alcohols, esters, or amides. When, however, the corresponding carboxylic acids are desired, these acids are prepared by hydrolysis of the corresponding ester using conventional methods. For example, the hydrolysis proceeds by reacting the esterified form of the prostacyclin analog with base in a water-alkanol mixture. Thus, sodium hydroxide and methanol is employed to hydrolyze the ester to the corresponding sodium salt.

The pharmacologically acceptable salts of these carboxylic acids are then obtained by neutralization with a corresponding base. Conventional techniques of isolation and recovery of the salt are employed.

When the acid addition salts are desired, reaction of the prostacyclin analog with the acid corresponding to the acid addition salt to be prepared yields the desired product.

With respect to the novel PG-type amides ($X_1$ is -$COL_4$) and p-substituted phenyl esters ($R_1$ is p-substituted phenyl, such compounds are prepared as follows:

With regard to the preparation of the p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amino and cycloamino derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the PG-type carboxylic acids, the corresponding carboxyamides are then prepared by one of several amidation methods known in the prior art. See, for example, U.S. Pat. No. 3,981,868, issued Sept. 21, 1976 for a description of the preparation of the present amino and cycloamino derivatives of prostaglandin-type free acids and U.S. Pat. No. 3,954,741, describing the preparation of carbonylamino and sulfonylamino derivatives of prostaglandin-type free acids.

The preferred method by which the present amino and cycloamino derivatives of the novel prostacyclin type free acids are prepared is, first by transformation of such free acids to corresponding mixed acid anydrides. By this procedure, the prostaglandin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the PGF-type free acid is mixed with both the tertiary amine base and the chloroformate in a suitable solvent (e.g., aqueous tetrahydrofuran), allowing the reaction to proceed at −10° to 20° C.

Thereafter, the mixed anhydride is converted to the corresponding amino or cycloamino derivative by reaction with the amine corresponding to the amide to be prepared. In the case where the simple amide (-NH$_2$) is to be prepared, the transformation proceeds by the addition of ammonia. Accordingly, the corresponding amine (or ammonia) is mixed with the mixed anhydride at or about −10° to +10° C., until the reaction is shown to be complete. For highly volatile amines, acid addition salts thereof (e.g., methylamine hydrochloride) are employed in place of the corresponding free base (e.g., methylamine).

Thereafter, the novel PGP-type amino or cycloamino derivative is recovered from the reaction mixture by conventional techniques.

The carbonylamino and sulfonylamino derivatives of the presently disclosed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl or sulfonyl isocyanate, corresponding to the carbonylamino or sulfonylamino derivative to be prepared.

By another, more preferred method the sulfonylamino derivatives of the present compounds are prepared by first generating the PG-type mixed anhydride, employing the method described above for the preparation of the amino and cycloamino derivatives. Thereafter, the sodium salt of the corresponding sulfonamide is reacted with the mixed anhydride and hexamethylphosphoramide. The pure PG-type sulfonylamino derivative is then obtained from the resulting reaction mixture by conventional techniques.

The sodium salt of the sulfonamide corresponding to the sulfonylamino derivative to be prepared is generated by reacting the sulfonamide with alcoholic sodium methoxide. Thus, by a preferred method methanolic sodium methoxide is reacted with an equal molar mount of the sulfonamide. The sulfonamide is then reacted, as described above, with the mixed anhydride, using about four equivalents of the sodium salt per equivalent of anhydride. Reaction temperatures at or about 0° C. are employed.

With regard to the phenacyl or substituted phenacyl esters herein, see U.S. Pat. No. 3,979,440 for a description of their preparation.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 infrared spectrophotometer.

Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer or an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

THF refers to tetrahydrofuran.

Specific Rotations, [α], are determined for solutions of a compound in the specified solvent at ambient temperature with a Perkin-Elmer Model 141 Automatic Polarimeter.

EXAMPLE 1: trans-4,5-Didehydro-6β-PGI$_1$, methyl ester (IV: X$_1$ is —COOCH$_3$, Z$_1$ is —(CH$_2$)$_2$—Z$_2$ is

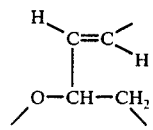

p and q are zero, R$_8$ is hydroxy, Y$_1$ is trans—CH═CH—, R$_3$ and R$_4$ of the L$_1$ moiety and R$_5$ of the M$_1$ moiety are all hydrogen, and R$_7$ is n-butyl), its 6α-isomer, and its corresponding free acid.

Refer to Chart A.

A. Molecular oxygen at ambient temperature is passed through a stirred solution of 4.7 g. of PGF$_2$α, methyl ester, 11,15-bis(α-ethoxyethyl ether), 0.206 g. of palladium acetate, and 1.833 g. of copper II acetate in 46 ml. of methanol and 3.7 ml. of water for 2.5 hours. Additional palladium acetate (0.206 g.) is then added and after an additional 2.5 hours the resulting mixture is filtered through diatomaceous earth and the filter solids washed with methanol and ethyl acetate. The combined filtrate is then evaporated under reduced pressure and the residue taken up in ethyl acetate and water (100 ml. each). The aqueous layer is then extracted with ethyl acetate and the combined organic extract is then washed with brine, dried over magnesium sulfate, and concentrated to yield 5.05 g. of crude trans-4,5-didehydro-PGI$_1$, methyl ester, 11,15-bis(α-ethoxyethyl ether) as a brown oil. The brown oil is then chromatographed on 500 g. of silica gel, packed and eluted with 30% ethyl acetate and Skellysolve B, yielding 2.77 g. of pure intermediate. NMR absorptions are observed at 5.85–5.2, 5.0–2.9, 3.65, and 2.4δ.

B. The reaction product of Part A (3.27 g.) in a mixture of 19 ml. of tetrahydrofuran, 38 ml. of water, and 114 ml. of ethyl acetate is heated to 40° C. for 4 hours.

The resulting mixture is then diluted with 350 ml. of water and lyophilized. The residue is then dissolved in diethyl ether and washed with 1 normal aqueous potassium bicarbonate and brine. Ethereal extracts are then dried over magnesium sulfate and concentrated to yield 2.2 g. of crude trans-4,5-didehydro-PGI$_1$, methyl ester as an oil. This oil is then chromatographed on 50 g. of silica gel, packed and eluted with 50% acetone in methylene chloride, yielding 2.06 g. of 6α- and 6β-epimerically mixed title product. A 1.25 g. sample of the epimeric mixture is then chromatographed on 200 g. of silica gel eluting with 30% acetone in methylene chloride, yielding a 0.46 g. sample enriched in the less polar, 6α-isomer. This 6α enriched sample is then rechromatographed on 2 silica columns in series using a 50% acetone in hexane diluent to yield 0.14 g. of pure trans 4,5-didehydro-6α-PGI$_1$, methyl ester as a waxy solid. Melting point is 63°–73° C. Elemental Analysis: Found C,68.45; H, 9.57. Infrared absorptions are observed at 3500, 3420, 1735, 1720, 1315, 1260, 1210, 1080, 1050, 1025, and 970 cm$^{-1}$. The mass spectrum for the trimethylsilyl derivative exhibits a high resolution peak at 510.3183 and other peaks at 495, 479, 439, 420, 349, 323, 199, and 173. NMR absorptions are observed at 5.8–5.4, 4.45–2.7, 3.67, and 2.4δ. Silica gel TLC Rf is 0.41 in acetone and methylene chloride (1:1).

From the original chromatographic separation a 0.89 g. sample of about 90% pure trans-4,5-didehydro-6β-PGI$_1$, methyl ester is rechromatographed on two silica columns in series eluting with 50% acetone in methylene chloride to yield 0.375 g. of 99% pure 6β-product and 0.359 g. of pure 6β-product as oils. NMR absorptions are observed at 5.8–5.3, 4.65–2.9, 3.63, and 2.36δ. The mass spectrum for the trimethylsilyl derivative exhibits a high resolution peak at 510.3193 and other peaks at 495, 479, 439, 420, 354, 307, and 173. Silica gel TLC Rf is 0.36 in acetone and methylene chloride (1:1).

C. The reaction product of Part B (the 6β-isomer, 0.42 g.) in 20 ml. of 95% aqueous ethanol is purged with nitrogen and 4 ml. of 1 N aqueous sodium hydroxide is added. After 2.5 hours at ambient temperature the resulting mixture is then concentrated under reduced pressure and the residue dissolved in water. The aqueous solution is then acidified with potassium bisulfate (0.6 g.) and extracted with ethyl acetate. The organic extracts are then washed with brine, dried over magnesium sulfate, concentrated to yield a colorless oil containing crude title free acid. Chromatographing on 50 g. of acid-washed silica gel packed with 20% acetone in methylene chloride and eluted with 20–60% acetone in methylene chloride yields 0.33 g. of pure title free acid as a yellow oil. The mass spectrum for the trimethylsilyl derivative exhibits high resolution peak at 568.3454 and other peaks at 553, 497, 478, 463, 407, 399, 279, 225, 199, 173, and 117.

Following the procedure of Example 1 but employing each of the various formula XXI PGF$_2$α, cis-4,5-didehydro-PGF$_1$α (q is 1), or 9,11-deoxy-9α-hydroxymethyl PGF$_2$, compounds of formula XXI in place of PGF$_2$α, methyl ester, there are prepared each of the corresponding formula XXIII trans 4,5-didehydro-6α- or 6β- PGI$_1$ type products as methyl esters or free acids.

EXAMPLE 2: trans-4,5,13,14-Tetradehydro-6β-PGI$_1$ methyl ester (Formula V: X$_1$ is —COOCH$_3$, Z$_1$ is —(CH$_2$)$_2$—, Z$_2$ is

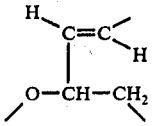

p and q are zero, R$_8$ is hydroxy, R$_3$ and R$_4$ of the L$_1$ moiety and R$_5$ of the M$_1$ moiety are all hydrogen, and R$_7$ is n-butyl) and its free acid.

Refer to Chart B.

A. A solution of 14-bromo-PGF$_2$α, methyl ester (1.9 g.) in methylene chloride (30 ml.) is added to a suspension of molecular iodine (2.85 g.), potassium iodide (1.80 g.), sodium acetate (0.92 g.), and water (6 ml.). The resulting mixture is then stirred for 2 hours, treated with 2 N aqueous sodium sulfite (20 ml.), washed successively with 5% aqueous sodium bicarbonate and 5% aqueous sodium chloride, dried, and concentrated to yield 2.95 g. of crude 9-deoxy-6,9α-epoxy-5-iodo-14-bromo-PGF$_1$α, methyl ester. A 0.13 g. aliquot of crude product is chromatographed on 13 g. of acid-washed silica gel, eluting with ethyl acetate and benzene (3:7), to yield 0.088 g. of pure formula XXXII product. NMR absorptions are observed at 0.89, 1.1–3.18, 3.66, 3.6–4.8, and 5.88δ. The mass spectrum for the trimethylsilyl derivative exhibits a high resolution peak at 701.1183, a molecular ion at 716, and other peaks at 645, 637, 589, 547, 529, 510, and 173. Infrared absorptions are observed at 3380, 1740, 1655, 1230, 1170, 1080, and 1050 cm$^{-1}$.

B. The reaction product of Part A (1.0 g. of crude, unchromatographed product) in methylene chloride (10 ml.) is treated with dihydropyran (3 ml.) and a 3 ml. solution of methylene chloride saturated with pyridine hydrochloride. After 20 hours the resulting mixture is then diluted with diethyl ether, washed successively with 5% aqueous sodium bicarbonate and 5% aqueous sodium chloride, dried, and concentrated to a 1.12 g. residue of 9-deoxy-6,9α-epoxy-5-iodo-14-bromo-PGF$_1$α, methyl ester, 11,15-bis(tetrahydropyranol ether). NMR absorptions are observed at 0.9, 1.05–2.20, 2.2–3.2, 3.2–4.35, 3.66, 4.35–4.15, and 5.7–6.1δ. Infrared absorptions are observed at 2900, 2820, 1760, 1440, 1350, 1210, 1125, 1090, 1035, 1025, 970, and 910 cm$^{-1}$.

C. A solution of 1.1 g. of the reaction product in Part B in dimethyl sulfoxide (15 ml.) and methanol (1.5 ml) is treated with potassium tert-butoxide (0.504 g.) for 20 hours. The resulting dark solution is then diluted with water (60 ml.), cooled, acidified with 5% aqueous phosphoric acid, and extracted with diethyl ether. Ethereal extracts are then washed with brine, dried, and concentrated to yield 0.173 g. of crude trans-4,5,13,14-tetradehydro-6β PGI$_1$, 11,15-bis(tetrahydropyranyl ether), which is esterified with excess ethereal diazomethane yielding the formula, XXXIV product. This crude formula XXXIV product exhibits characteristic NMR absorptions at 5.5–5.8 and 2.41δ.

D. The crude reaction product of Part C (0.168 g.) in acetic acid (6 ml.) is treated with water (3 ml.) at 40° C. for 3 hours. The resulting solution is then extracted with 250 ml. of methanol and concentrated to yield 0.106 g. of crude title methyl ester as a yellow residue.

Chromatographing on 50 g. of silica gel, eluting with Skellysolve B and ethyl acetate (1:1) yielding 76.1 mg. of pure methyl ester. The mass spectrum for the trimethylsilyl derivative exhibits a high resolution peak at 508.3025 and additional peak at 421.

E. A solution of the reaction product of Part B (3 g.) in a mixture of dimethyl sulfoxide and methanol (17:3, 10 ml.) is treated with potassium tert-butoxide (1.69 g.) in the same dimethylsulfoxide-methanol mixture (35 ml.). After 14 hours additional potassium tert-butoxide (0.85 g.) is added and the reaction maintained for an additional 21 hours. The resulting mixture is then quenched by addition of 2 N aqueous sodium hydroxide (20 ml.) and water (20 ml.). After an additional 12 hours the resulting mixture is cooled, yielding a semi-solid residue which is acidified with phosphoric acid at 0° C. and extracted with ethyl acetate. The ethereal extracts are then washed with 5% aqueous sodium chloride, dried, and concentrated to yield 2.116 g. of crude trans-4,5,13,14-tetradehydro-6$\beta$-PGI$_1$, 11,15-bis(tetrahydropyranyl ether). This crude title product is then chromatographed on acid-washed silica gel (170 g.) eluting with mixtures of Skellysolve B and ethyl acetate, to yield 0.3326 g. of pure bis(tetrahydropyranyl ether).

F. A solution of 0.33 g. of the reaction product of Part E in acetic acid (20 ml.) is treated with water (10 ml.) at 40° C. for 3.5 hours. The resulting mixture is then diluted with water (25 ml.) and lyophilized to a yellow residue. This residue is then chromatographed on acid-washed silica gel (60 g.) eluting with mixtures of ethyl acetate and hexane to yield 0.0925 g. of pure title free acid.

Following the procedure of Part B, there are obtained each of the various formula XXXV products from the corresponding formula a XXXI PGF-type compounds in free acid or ester form.

EXAMPLE 4:
trans-4,5,13,14-Tetradehydro-15-epi-6$\beta$-PGI$_1$ (Formula V as in Example 2 except that the hydroxy of the M$_1$ moiety is in the beta configuration).

Refer to Chart B.

A. Following the procedure of Example 2, Parts A and B, 15-epi-14-bromo-PGF$_2\alpha$, methyl ester is transformed to 9-deoxy-6,9$\alpha$-epoxy 5-iodo-14-bromo-15-ept-PGF$_1\alpha$, methyl ester, 11,15-bis(tetrahydropyranyl ether).

B. A solution of the reaction product of Part A (0.350 g.) is transformed according to the procedure of Example 2, Part F to 90.5 mg. of pure title product.

EXAMPLE 5: trans, trans-2,3,4,5-Tetradehydro-PGI$_1$, methyl ester (Formula VI: X$_1$ is —COOCH$_3$, $p$ and $q$ are zero, R$_8$ is hydroxy, Y$_3$ is trans—CH=CH—, R$_3$ and R$_4$ are the L$_1$ moiety and R$_5$ of the M$_1$ moiety are all hydrogen, and R$_7$ is n-butyl) and its free acid.

Refer to Chart C.

A. 9-Deoxy-6,9$\alpha$-epoxy-5-iodo PGF$_1\alpha$, methyl ester (2 g., prepared according to procedure of Example 2, Part A from PGF$_2\alpha$, methyl ester) is dissolved in 26 ml. of tetrahydropyran at ambient temperature. Thereafter, hexamethyldisilane (4.6 ml.) is added, followed by addition of 1.2 ml. of trimethylsilyl chloride. In about 10 to 15 minutes a white precipitate forms and concentration under reduced pressure and filtration through diatomaceous earth followed by a second concentration yields 2.42 g. of 9-deoxy-6,9$\alpha$-epoxy-5-iodo PGF$_1\alpha$, methyl ester, 11,15-bis(trimethylsilyl ether), a formula XLIII compound.

B. A mixture of N-isopropylcyclohexylamine in 30 ml. of tetrahydrofuran cooled to −28° C. for 15 minutes is added the reaction product of Part A (2.4 g.) in 20 ml. of tetrahydrofuran. Thereafter 1.6 molar n-butyllithium in hexane (4.7 ml.) is added and the resulting mixture stirred for 30 minutes. Thereafter diphenylselenide (1.76 g.) in 15 ml. of tetrahydrofuran is added at −78° C. and stirring is continued at this temperature for an additional hour. The resulting mixture is then allowed to warm to 0° C. and poured into ammonium chloride (150 ml.) in diethyl ether (150 ml.). Extraction with diethyl ether and washing of the ethereal extracts with water and brine, drying over sodium sulfate, and concentrating under reduced pressure yields 4.10 g. of crude 9-deoxy-6.9$\alpha$-epoxy-2-phenylselenyl-5-iodo-PGF$_1\alpha$, methyl ester 11,15-bis(trimethylsilyl ether).

C. The crude reaction product of Part B (2.98 g.) is then stirred with 80 ml. of a methanol and citric acid mixture (3:1) for 30 minutes. Thereafter the solution was decanted and 50 ml. of methanol added and the resulting mixture concentrated under reduced pressure and the residue dissolved in methylene chloride, washed with water, dried, and concentrated to yield 3.81 g. of crude formula XLV product: 9-deoxy-6,9$\alpha$-epoxy-2-phenylselenyl-5-iodo-PGF$_1\alpha$, methyl ester. This crude product is then purified by chromatographing on 350 g. of silica gel, eluting with acetone and methylene chloride mixtures to yield 1.87 g. of pure product.

D. Thirty percent aqueous hydrogen peroxide (3.29 g.) is added to the reaction product Part C in 65 ml. of methylene chloride at ambient temperature. Vigorous stirring is initiated for 1 hour, whereupon the layers are separated and the organic layer is washed with 5% aqueous sodium bicarbonate, saturated sodium bicarbonate, and brine. The aqueous washings are then extracted with methylene chloride and the combined organic extracts are then dried yielding 1.5 g. of crude formula XLVI compound: 9-deoxy-6,9$\alpha$-epoxy trans-2,3-didehydro-5-iodo-PGF$_1\alpha$, methyl ester. This crude product is then chromatographed on 20 g. of silica gel eluting with acetone and diethyl ether (1:2) to yield 540 mg. of pure formula XLVI product. The high resolution mass spectrum for the trimethylsilyl derivative exhibits a peak at 637.1876 and other peaks are observed at 652, 749, 363, and 173.

E. Thirty-three ml. of dry benzene and 1.2 ml. of dry DBN at ambient temperature are combined with 590 mg. of the reaction product of Part D at 40° C. for 30 min. Thereafter, the reaction mixture is washed with water, dried, and concentrated to yield 497 mg. of crude title methyl ester. This crude product is then chromatographed on 60 g. of silica gel eluting with acetone and methylene chloride to yield 427 mg. of pure title methyl ester as a yellow oil. The mass spectrum exhibits a high resolution peak for this trimethylsilyl derivative at 508.3040 and other peaks are observed at 493, 477, 437, 418, 403, 347, and 328. Specific optical rotation is +51° at 5.1 g.ml. in chloroform.

F. The reaction product of Part E (100 mg.) in 3 ml. of methanol at ambient temperatures is combined with 0.95 ml. of 3 N aqueous potassium hydroxide with stirring. After 1.5 hours at ambient temperature and an additional hour at 50° C. 67 mg. of potassium t-butoxide in methanol is added and the reaction continued at ambient temperature. Thereupon a mixture of 75 ml. of ethanol and 5 ml. of 2 N aqueous potassium bisulfate is added adjusting pH to about 3. Upon addition of 20 ml. of water the organic and aqueous layers are separated and the aqueous layer is saturated with sodium chloride and extracted with ethyl acetate. The combined organic extracts are then dried and concentrated yielding 44 mg. of title free acid. The high resolution mass spectrum for the trimethylsilyl derivative exhibits a peak at 566.3282 and other peaks are observed at 551, 495, 426, 405, and 356.

Following the procedure of Example 4, the various formula XLI compounds are transformed to corresponding formula XLVII esters and formula XLVIII acids.

Further, the resulting formula XLVII acids are reduced to the corresponding formula XLVIII primary alcohols with lithium aluminum hydride and the formula XLIX esters transformed to the formula L amides by amidization methods described above. Finally, the formula L amides are reduced with lithium aluminum hydride to the corresponding formula LI primary amines which are thereafter mono or dialkylated by methods known in the art.

Likewise, the acids and esters described in and following Examples 1–4 are transformed to corresponding amides, primary alcohols, or amines as described above.

EXAMPLE 6: trans-4,5-Didehydro-6$\beta$-PGI$_1$, p-phenylphenacyl ester and its 6$\alpha$ isomer A. trans-4,5-Didehydro-6$\alpha$-PGI$_1$, 25 ml. of methyl cyanide, 1.5 g. of p-phenylphenacyl bromide and 1 ml. of diisopropylethylamine are combined at ambient temperature for 1 hr. and thereafter diluted with potassium bisulfate and ethyl acetate. The ethyl acetate extracts are then washed with brine, dried over magnesium sulfate, and concentrated to yield 0.44 g. of an oil which crystallizes on standing. Recrystallization from methyl acetate yields 0.26 g. of pure trans-4,5-didehydro-6$\alpha$-PGI$_1$, p-phenylphenacyl ester, 0.26 g. Melting point is 92–96° C. The mass spectrum exhibits a high resolution peak for the trimethylsilyl derivative at 690.3749 and infrared absorptions are observed at 3450, 1735, 1710, 1610, 1460, 1375, 1235, 1170, 1050, 965, 890, 835, and 765 cm$^{-1}$.

B. Following the procedure of Part A, trans-4,5-didehydro-6$\beta$-PGI$_1$ is transformed to 0.65 g. of crystalline 6$\beta$ title product. Recrystallization from ethyl acetate and hexane yields 0.38 g. of pure 6$\beta$ isomer. Melting point is 105–107° C. NMR absorptions are observed at 7.2-8.1, 5.4-5.75, 5.3, 3.5-4.7, and 0.98. Infrared absorptions are observed at 3450, 1740, 1715, 1615, 1460, 1375, 1240, 1170, 790, 840, 765, 725, and 690 cm$^{-1}$.

Following the procedure of the above examples, but employing the appropriate PGF$_2\alpha$-type, cis-4,5-didehydro-PGF$_2\alpha$-type or 9-deoxy-9-hydroxymethyl-PGF$_2\alpha$-type starting material, there are prepared trans-4,5-didehydro-6$\alpha$-PGI$_1$-type compounds;
trans-4,5-didehydro-6$\alpha$-PGI$_1$-type compounds;
trans,trans-2,3,4,5-tetradehydro-6$\alpha$-PGI$_1$-type compounds;
trans,trans-2,3,4,5-tetradehydro-6$\beta$-PGI$_1$-type compounds;
7a-homo-trans-4,5-didehydro-6$\alpha$-PGI$_1$-type compounds;
7a-homo-trans-4,5-didehydro-6$\beta$-PGI$_1$-type compounds;
7a-homo-trans,trans-2,3,4,5-tetradehydro-6$\alpha$-PGI$_1$-type compounds;
7a-homo-trans,trans-2,3,4,5-tetradehydro-6$\beta$-PGI$_1$-type compounds;
(6R)- or (6S)-trans-4,5-didehydro-9-deoxy-6,9$\alpha$-epoxymethylene-PGF$_1$-type compounds; or
(6R)- or (6S)-trans,trans-2,3,4,5-tetradehydro-9-deoxy-6,9$\alpha$-epoxymethylene-PGF$_1$-type compounds in free acid, amide, or ester form which exhibit the following side chain substituents:

15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;
16-Phenyl-18,19,20-trinor-13,14,-didehydro-;
16-Methyl-16-phenyl-18,19,20-trinor-13,14-didehydro-;
16-Phenoxy-17,18,19,20-tetranor-13,14-didehydro-;

16-(m-trifluoromethylphenoxy)-17,18,19,20-tetranor-13,14-didehydro-;
16(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
13-cis-;
16-Methyl-13-cis-;
16,16-Dimethyl-13-cis-;
16-Fluoro-13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16-Phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-Phenyl-18,19,20-trinor-13-cis-;
16-Methyl-16-phenyl-18,19,20-trinor-13-cis-;
16-Phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-fluorophenoxy)-17,18,19,20-tetranor-13-cis-;
16-Phenoxy-18,19,20-trinor-13-cis-;
16-Methyl-16-phenoxy-18,19,20,-trinor-13-cis-;
2,2-Difluoro-;
2,2-Difluoro-15-methyl-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,19,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-
2,2-Difluoro-16-(p-fluorophenoxy)-17,18,19,20-tetranor-
2,2-Difluoro-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Diflouro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-phenyl-18,19,20-trinor-13,14-didehydro-
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;

2,2-Difluoro-16-phenoxy-18,19,20-trinor-13,14-didehydro
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14-dihydro-;
2,2-Difluoro-16-(m-trifluoromethylphenyl)-17,18,19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)-17,18,19,20-tetranor-13,14-dihydro-;
2,2-Difluoro-16-phenyl-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxyl)-17,18,19,20tetranor-13,14-dihydro-;
2,2-Difluoro-16-(m-chlorophenoxy)-17,18,19,20-tetranor 13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
2,2-Difluoro-13-cis-;
2,2-Difluoro-16-methyl-13-cis-;
2,2-Difluoro-16,16-dimethyl-13-cis-;
2,2,16-Trifluoro-13-cis-;
2,2,16,16-Tetrafluoro-13-cis-;
2,2-Difluoro-17-phenyl-18,19,20-trinor-13-cis-;
2,2-Difluoro-17-(m-trifluoromethylphenyl)-18,19,20-trinor-13-cis-;
2,2-Difluoro-17-(m-chlorophenyl)-18,19,20-trinor-13-cis-;
2,2-Difluoro-17-(p-fluorophenyl)-18,19,20-trinor-13-cis-;
2,2-Difluoro-16-(methyl-17-phenyl-18,19,20-trinor-13-cis-;
2,2-Difluoro-16,16-dimethyl-17-phenyl-18,19,20-trinor-13-cis-;
2,2,16-Trifluoro-17-phenyl-18,19,20-trinor-13-cis-;
2,2,16,16-Tetrafluoro-17-phenyl-18,19,20-trinor-13-cis-;
2,2-Difluoro-16-phenyl-17,18,19,20-tetranor-13-cis-;
2,2-Difluoro-16-(m-trifluoromethylphenyl)-17,18,19,20-tetranor-13-cis-;
2,2-Difluoro-16-(m-chlorophenyl)-17,18,19,20-tetranor-13-cis-;
2,2-Difluoro-16-(p-fluorophenyl)-17,18,19,20-tetranor-13-cis-;
2,2-Difluoro-16-phenyl-18,19,20-trinor-13-cis-;
2,2-Difluoro-16-methyl-16-phenyl-18,19,20-trinor-13-cis-;
2,2-Difluoro-16-phenoxy-17,18,19,20-tetranor-13-cis-;
2,2-Difluoro-16-(m-trifluoromethylphenoxy)-17,18,19,20-tetranor-13-cis-;
2,2-Difluoro-16-(m-chlorophenoxy)-17,18,19,20-tetranor-13-cis-;
2,2-Difluoro-16-(p-fluorophenoxy)-17,18,19,20-tetranor-13-cis-;
2,2-Difluoro-16-phenoxy-18,19,20-trinor-13-cis-;
2,2-Difluoro-16-methyl-16-phenoxy-18,19,20-trinor-13-cis;
trans-2,3-Didehydro-;
trans-2,3-Didehydro-15-methyl-;
trans-2,3-Didehydro-16-methyl-;
trans-2,3-Didehydro-16,16-dimethyl-;
trans-2,3-Didehydro-16-fluoro-;
trans-2,3-Didehydro-16,16-difluoro-;
trans-2,3-Didehydro-17-phenyl-18,19,20-trinor-;
trans-2,3-Didehydro-17-(m-trifluoromethylphenyl)-18,19,20-trinor-;
trans-2,3-Didehydro-17-(m-chlorophenyl)-18,19,20-trinor-;
trans-2,3-Didehydro-17-(p-fluorophenyl)-18,19,20-trinor-;
trans-2,3-Didehydro-16-methyl-17-phenyl-18,19,20-trinor-;
trans-2,3-Didehydro-16,16-dimethyl-17-phenyl-18,19,20-trinor-;
trans-2,3-Didehydro-16-fluoro-17-phenyl-18,19,20-trinor-;
trans-2,3-Didehydro-16,16-difluoro-17-phenyl-18,19,20-trinor-;
trans-2,3-Didehydro-16-phenyl-17,18,19,20-tetranor-;
trans-2,3-Didehydro-16-(m-trifluoromethylphenyl)-17,18,19,20-tetranor-;
trans-2,3-Didehydro-16-(m-chlorophenyl)-17,18,19,20-tetranor-;
trans-2,3-Didehydro-16-(p-fluorophenyl)-17,18,19,20-tetranor-;
trans-2,3-Didehydro-16-phenyl-18,19,20-trinor-;
trans-2,3-Didehydro-16-methyl-16-phenyl-18,19,20-trinor-;
trans-2,3-Didehydro-16-phenoxy-17,18,19,20-tetranor-;
trans-2,3-Didehydro-16-(m-trifluoromethylphenoxy)-17,18,19,20-tetranor-;
trans-2,3-Didehydro-16-(m-chlorophenoxy)-17,18,19,20-tetranor-;
trans-2,3-Didehydro-16-(p-fluorophenoxy)-17,18,19,20-tetranor-;
trans-2,3-Didehydro-16-phenoxy-18,19,20-trinor-;
trans-2,3-Didehydro-16-methyl-16-phenoxy-18,19,20-trinor-;
trans-2,3-Didehydro-13,14-didehydro-;
trans-2,3-Didehydro-16-methyl-13,14-didehydro-;
trans-2,3-Didehydro-16,16-dimethyl-13,14-didehydro-;
trans-2,3-Didehydro-16-fluoro-13,14-didehydro-;
trans-2,3-Didehydro-16,16-difluoro-13,14-didehydro-;
trans-2,3-Didehydro-17-phenyl-18,19,20-trinor-13,14-didehydro-;

trans-2,3-Didehydro-17-(m-trifluoromethylphenyl)-18,19,20-trinor-13,14-didehydro-;
trans-2,3-Didehydro-17-(m-chlorophenyl)-18,19,20-trinor-13,14-didehydro-;
trans-2,3-Didehydro-17-(p-fluorophenyl)-18,19,20-trinor-13,14-didehydro-;
trans-2,3-Didehydro-16-methyl-17-phenyl-18,19,20-trinor-13,14-didehydro-;
trans-2,3-Didehydro-16,16-dimethyl-17-phenyl-18,19,20-trinor-13,14-didehydro-;
trans-2,3-Didehydro-16-fluoro-17-phenyl-18,19,20-trinor-13,14-didehydro-;
trans-2,3-Didehydro-16,16-difluoro-17-phenyl-18,19,20-trinor-13,14-didehydro-;
trans-2,3-Didehydro-16-phenyl-17,18,19,20-tetranor-13,14-didehydro-;
trans-2,3-Didehydro-16-(m-trifluoromethylphenyl)-17,18,19,20-tetranor-13,14-didehydro-;
trans-2,3-Didehydro-16-(m-chlorophenyl)-17,18,19,20-tetranor-13,14-didehydro-;
trans-2,3-Didehydro-16-phenyl-18,19,20-trinor-13,14-didehydro-;
trans-2,3-Didehydro-16-methyl-16-phenyl-18,19,20-trinor-13,14-didehydro-;
trans-2,3-Didehydro-16-phenoxy-17,18,19,20-tetranor-13,14-didehydro-;
trans-2,3-Didehydro-16-(m-trifluoromethylphenoxy)-17,18,19,20-tetranor-13,14-didehydro-;
trans-2,3-Didehydro-16-(m-chlorophenoxy)-17,18,19,20-tetranor-13,14-didehydro-;
trans-2,3-Didehydro-16-phenoxy-18,19,20-trinor-13,14-didehydro-;
trans-2,3-didehydro-16-methyl-16-phenoxy-18,19,20-trinor-13,14-didehydro-;
trans-2,3-Didehydro-13,14-dihydro-;
trans-2,3-Didehydro-16-methyl-13,14-dihydro-;
trans-2,3-Didehydro-16,16-dimethyl-13,14-dihydro-;
trans-2,3-Didehydro-16-fluoro-13,14-dihydro-;
trans-2,3-Didehydro-16,16-difluoro-13,14-dihydro-;
trans-2,3-Didehydro-17-phenyl-18,19,20-trinor-13,14-dihydro-;
trans-2,3-Didehydro-17-(m-trifluoromethylphenyl)-18,19,20-trinor-13,14-dihydro-;
trans-2,3-Didehydro-17-(m-chlorophenyl)-18,19,20-trinor-13,14-dihydro-;
trans-2,3-Didehydro-17-(p-fluorophenyl)-18,19,20-trinor-13,14-dihydro-;
trans-2,3-Didehydro-16-methyl-17-phenyl-18,19,20-trinor-13,14-dihydro-;
trans-2,3-Didehydro-16,16-dimethyl-17-phenyl-18,19,20-trinor-13,14-dihydro-;
trans-2,3-Didehydro-16-fluoro-17-phenyl-18,19,20-trinor-13,14-dihydro-;
trans-2,3-Didehydro-16,16-difluoro-17-phenyl-18,19,20-trinor-13,14-dihydro-;
trans-2,3-Didehydro-16-phenyl-17,18,19,20-tetranor-13,14-dihydro-;
trans-2,3-Didehydro-16-(m-trifluoromethylphenyl)-17,18,19,20-tetranor-13,14-dihydro-;
trans-2,3-Didehydro-16-(m-chlorophenyl)-17,18,19,20-tetranor-13,14-dihydro-;
trans-2,3-Didehydro-16-(p-fluorophenyl)-17,18,19,20-tetranor-13,14-dihydro-;
trans-2,3-Didehydro-16-phenyl-18,19,20-trinor-13,14-dihydro-;
trans-2,3-Didehydro-16-methyl-16-phenyl-18,19,20-trinor-13,14-dihydro-;
trans-2,3-Didehydro-16-phenoxy-17,18,19,20-tetranor-13,14-dihydro-;
trans-2,3-Didehydro-16-(m-trifluoromethylphenoxy)-17,18,19,20-tetranor-13,14-dihydro-;
trans-2,3-Didehydro-16-(m-chlorophenoxy)-17,18,19,20-tetranor-13,14-dihydro-;
trans-2,3-Didehydro-16-(p-fluorophenoxy)-17,18,19,20-tetranor-13,14-dihydro-;
trans-2,3-Didehdyro-16-phenoxy-18,19,20-trinor-13,14-dihydro-;
trans-2,3-Didehydro-16-methyl-16-phenoxy-18,19,20-trinor-13,14-dihydro-;
trans-2,3-Didehydro-13-cis-;
trans-2,3-Didehydro-16-methyl-13-cis-;
trans-2,3-Didehydro-16,16-dimethyl-13-cis-;
trans-2,3-Didehydro-16-fluoro-13-cis-;
trans-2,3-Didehydro-16,16-difluoro-13-cis-;
trans-2,3-Didehydro-17-phenyl-18,19,20,-trinor-13-cis-;
trans-2,3-Didehydro-17-(m-trifluoromethylphenyl)-18,19,20-trinor-13-cis-;
trans-2,3-Didehydro-17-(m-chlorophenyl)-18,19,20-trinor-13-cis-;
trans-2,3-Didehydro-17-(p-fluorophenyl)-18,19,20-trinor-13-cis-;
trans-2,3-Didehydro-16-methyl-17-phenyl-18,19,20-trinor-13-cis-;
trans-2,3-Didehydro-16,16-dimethyl-17-phenyl-18,19,20-trinor-13-cis-;
trans-2,3-Didehydro-16-fluoro-17-phenyl-18,19,20-trinor-13-cis-;
trans-2,3-Didehydro-16,16-difluoro-17-phenyl-18,19,20-trinor-13-cis-;
trans-2,3-Didehydro-16-phenyl-17,18,19,20-tetranor-13,-cis-;
trans-2,3-Didehydro-16-(m-trifluoromethylphenyl)-17,18,19,20-tetranor-13-cis-;
trans-2,3-Didehydro-16-(m-chlorophenyl)-17,18,19,20-tetranor-13-cis-;
trans-2,3-Didehydro-16-(p-fluorophenyl)-17,18,19,20-tetranor-13-cis-;
trans-2,3-Didehydro-16-phenyl-18,19,20,-trinor-13-cis-;
trans-2,3-Didehydro-16-methyl-16-phenyl-18,19,20-trinor-13-cis-;
trans-2,3-Didehydro-16-phenoxy-17,18,19,20-tetranor-13-cis-;
trans-2,3-Didehydro-16-(m-trifluoromethylphenoxy)-17,18,19,20-tetranor-13-cis-;
trans-2,3-Didehydro-16-(m-chlorophenoxy)-17,18,19,20-tetranor-13-cis-;
trans-2,3-Didehydro-16-(p-fluorophenoxy)-17,18,19,20-tetranor-13-cis-;
trans-2,3-Didehydro-16-phenoxy-18,19,20,-trinor-13-cis-;
trans-2,3-Didehydro-16-methyl-16-phenoxy-18,19,20-trinor-13-cis-;
and their corresponding 11-deoxy-PGF$_1$ and 11-deoxy-11-hydroxymethyl-PGF$_1$ analogs.

Further following the procedures described above there is prepared the corresponding 2-decarboxy-2-hydroxymethyl type compounds by reduction of the corresponding carboxylic acid esters and the corresponding 2-decarboxy-2-aminomethyl type compound by reduction of the novel prostacyclin-type amides with lithium aluminum hydride. See especially U.S. Pat. No. 4,028,350, describing the preparation of C-1 amine and C-1 alcohol analogs of certain bicyclic prostaglandins. Further, for the above carboxylic acids, the corresponding pharmacologically acceptable salts are prepared by neutralization with the appropriate base. For the 2-decarboxy-2-aminomethyl-type compounds, pharmacologically acceptable acid addition salts are prepared by neutralization with the acid corresponding to the salt to be prepared.

I claim:
1. A prostacyclin analog of the formula

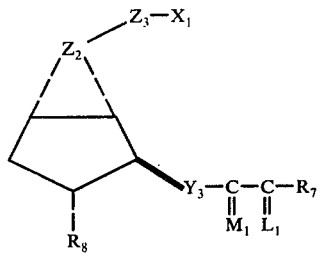

wherein $Z_3$ is trans—CH=CH—,
wherein $Y_3$ is
(1) trans—CH=CH—,
(2) cis—CH=CH—,
(3) —CH$_2$CH$_2$—, or
(4) —C≡C—
wherein $Z_2$ is

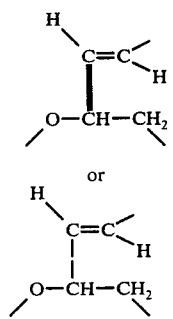

wherein $R_h$ is hydrogen, hydroxy, or hydroxymethyl;
wherein $M_1$ is

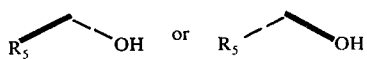

wherein $R_5$ is hydrogen or alkyl with one to 4 carbon atoms, inclusive,
wherein $L_1$ is

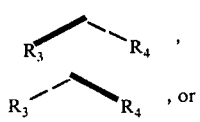

a mixture of

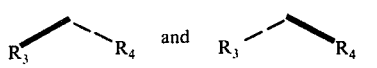

wherein $R_3$ and $R_4$ are hydrogen, methyl, or fluoro, being the same or different, with the proviso that one of $R_3$ and $R_4$ is fluoro only when the other is hydrogen or fluoro; wherein $X_1$ is
(1) —COOR$_1$ wherein $R_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

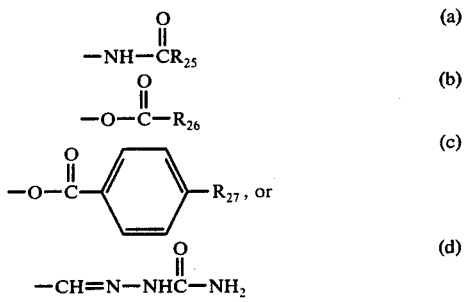

wherein $R_{25}$ is methyl, phenyl, acetamidophenyl, benzamidophenyl, or —NH$_2$; $R_{26}$ is methyl, phenyl, —NH$_2$, or methoxy; and $R_{27}$ is hydrogen or acetamido; inclusive, phenacyl, i.e.,

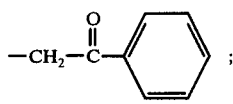

phenacyl substituted in the para position by chloro, bromo, phenyl, or benzamido; or a pharmacologically acceptable cation;
(2) —CH$_2$OH;
(3) —CH$_2$NL$_2$L$_3$ wherein $L_2$ and $L_3$ are hydrogen or alkyl of one to 4 carbon atoms, inclusive; or
(4) —COL$_4$, wherein $L_4$ is
(a) amino of the formula -NR$_{21}$R$_{22}$; wherein $R_{21}$ and $R_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy, carboxy, alkoxycarbonyl of one to 4 carbon atoms, inclusive, or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive or nitro; pyridyl; pyridyl substituted by one, 2, or 3 chloro, alkyl of one to 3 carbon atoms, inclusive or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms inclusive, hydroxy, or alkoxy of one to 3 carbon atoms, inclusive; hydroxyalkyl of one to 4 carbon atoms, inclusive; dihydroxyalkyl of one to 4 carbon atoms; and trihydroxyalkyl of one to 4 carbon atoms; with the further proviso that not more than one of $R_{21}$ and $R_{22}$ is other than hydrogen or alkyl;
(b) cycloamino selected from the group consisting of

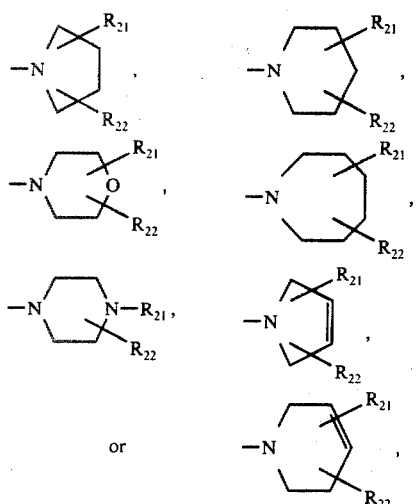

wherein $R_{21}$ and $R_{22}$ are as defined above;

(c) carbonylamino of the formula —$NR_{23}COR_{21}$, wherein $R_{23}$ is hydrogen or alkyl of one to 4 carbon atoms and $R_{21}$ is as defined above;

(d) sulphonylamino of the formula —$NR_{23}SO_2R_{21}$, wherein $R_{21}$ and $R_{22}$ are as defined above; or (e) hydrazino of the formula —$NR_{23}R_{24}$, wherein $R_{23}$ is as defined above and $R_{24}$ is amino of the formula —$NR_{21}R_{22}$, as defined above, or cycloamino, as defined above.

wherein $R_7$ is (1) —$(CH_2)_m$—$CH_3$,

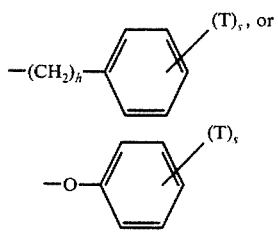

wherein $m$ is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that no more than two T's are other than alkyl; and the pharmacologically acceptable acid addition salts thereof when $X_1$ is —$CH_2NL_2L_3$.

2. A prostacyclin analog according to claim 1, wherein $R_8$ is hydroxymethyl.

3. 11-Deoxy-11-hydroxymethyl-trans,trans-2,3,4,5-tetradehydro-6β-PGI$_1$, a prostacyclin analog according to claim 2.

4. A prostacyclin analog according to claim 1, wherein $R_8$ is hydrogen.

5. 11-Deoxy-trans,trans-2,3,4,5-tetradehydro-6β-PGI$_1$, a prostacyclin analog according to claim 4.

6. A prostacyclin analog according to claim 1, wherein $R_8$ is hydroxy.

7. A prostacyclin analog according to claim 6, wherein $Z_2$ is a mixture of

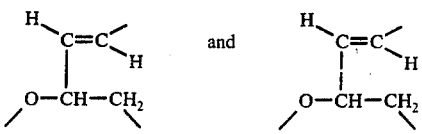

8. (6RS)-trans,trans-2,3,4,5-Tetradehydro-PGI$_1$, a prostacyclin analog according to claim 7.

9. A prostacyclin analog according to claim 6, wherein $Z_2$ is

10. trans,trans-2,3,4,5-Tetradehydro-6α-PGI$_1$, a prostacyclin analog according to claim 9.

11. 15-Methyl-trans,trans-2,3,4,5-tetradehydro-6α-PGI$_1$, a prostacyclin analog according to claim 9.

12. 16,16-Dimethyl-trans,trans-2,3,4,5-tetradehydro-6α-PGI$_1$, a prostacyclin analog according to claim 9.

13. 16,16-Difluoro-trans,trans-2,3,4,5-tetradehydro-6α-PGI$_1$, a prostacyclin analog according to claim 9.

14. A prostacyclin analog according to claim 6, wherein $Z_2$ is

15. A prostacyclin analog according to claim 14, wherein $Y_3$ is cis—CH=CH—.

16. cis-13-trans,trans,2,3,4,5-Tetradehydro-6α-PGI$_1$, a prostacyclin analog according to claim 15.

17. A prostacyclin analog according to claim 14, wherein $Y_3$ is -C≡C—.

18. trans,trans-2,3,4,5,13,14-hexadehydro-6α-PGI$_1$, a prostacyclin analog according to claim 17.

19. A prostacyclin analog according to claim 14, wherein $Y_3$ is —$CH_2CH_2$—.

20. 13,14-Dihydro-trans,trans-2,3,4,5-tetradehydro-6β-PGI$_1$, a prostaglandin analog according to claim 19.

21. 13,14-Dihydro-15-methyl-trans,trans-2,3,4,5-tetradehydro-6β-PGI$_1$, a prostacyclin analog according to claim 19.

22. 13,14-Dihydro-16,16-dimethyl-trans,trans-2,3,4,5-tetradehydro-6β-PGI$_1$, a prostacyclin analog according to claim 19.

23. A prostacyclin according to claim 14, wherein $Y_3$ is trans—CH=CH—.

24. A prostacyclin analog according to claim 23, wherein $R_7$ is

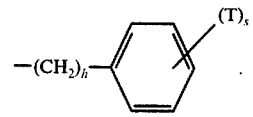

25. A prostacyclin analog according to claim 23, wherein $R_7$ is

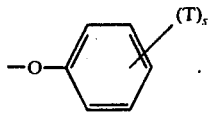

26. A prostacyclin analog according to claim 23, wherein $R_7$ is $-(CH_2)_m-CH_3-$.

27. A prostacyclin analog according to claim 26, wherein $m$ is 3.

28. A prostacyclin analog according to claim 27, wherein $X_1$ is $-COL_4$.

29. A prostacyclin analog according to claim 27, wherein $X_1$ is $CH_2OH-$.

30. A prostacyclin analog according to claim 27, wherein $X_1$ is $-COOR_1$.

31. A prostacyclin analog according to claim 30, wherein $R_5$ is methyl.

32. 15-Methyl-trans,trans-2,3,4,5-tetradehydro-6β-PGI$_1$, a prostacyclin analog according to claim 31.

33. A prostacyclin analog according to claim 30, wherein $R_5$ is hydrogen.

34. A prostacyclin analog according to claim 33, wherein at least one of $R_3$ and $R_4$ is fluoro.

35. 16,16-Difluoro-trans,trans-2,3,4,5-tetradehydro-6β-PGI$_1$, a prostacyclin analog according to claim 34.

36. A prostacyclin analog according to claim 33, wherein at least one of $R_3$ and $R_4$ is methyl.

37. 16,16-Dimethyl-trans,trans-2,3,4,5-tetradehydro-6β-PGI$_1$, a prostacyclin analog according to claim 36.

38. A prostacyclin analog according to claim 33, wherein $R_3$ and $R_4$ are both hydrogen.

39. trans,trans-2,3,4,5-Tetradehydro-6β-PGI$_1$, methyl ester, a prostacyclin analog according to claim 38.

40. trans,trans-2,3,4,5-Tetradehydro-6β-PGI$_1$, tris(hydroxymethyl)amino methane salt, a prostacyclin analog according to claim 38.

41. trans,trans-2,3,4,5-Tetradehydro-6β-PGI$_1$, adamantanamine salt, a prostacyclin analog according to claim 38.

42. trans,trans-2,3,4,5-Tetradehydro-6β-PGI$_1$, a prostacyclin analog according to claim 38.

* * * * *

UNITED STATES PATENT AND TRADEMARK OFFICE
CERTIFICATE OF CORRECTION

PATENT NO. : 4,109,082
DATED : August 22, 1978
INVENTOR(S) : John C Sih

It is certified that error appears in the above—identified patent and that said Letters Patent is hereby corrected as shown below:

Column 1, lines 17-32, that portion of the formula reading

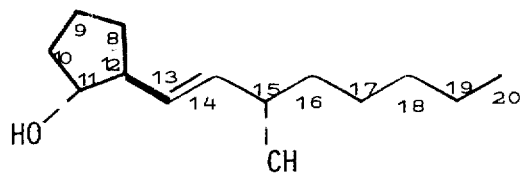   should read   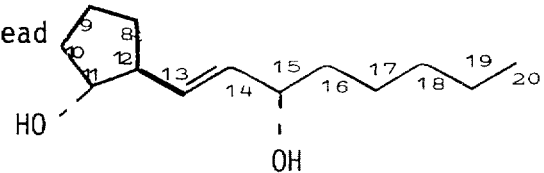

Column 3, line 50, "wherein one p and q is" should read -- wherein one of p and q is --;
Column 4, line 60, "phenyl phenyl substituted" should read -- phenyl; phenyl substituted --;
Column 5, line 45, "wherein $R_{21}$ and $R_{22}$" should read -- wherein $R_{21}$ and $R_{23}$ --;
Column 6, line 19, "$X_1$ is $-CH_2CH_{NL_2}L_3$" should read -- $X_2$ is $-CH_2NL_2L_3$ --;
Column 10, line 13, "(o-, m-, or p-methoxyphenyl," should read -- (o-, m-, or p-)methoxyphenyl, --;
Column 11, line 53, "γ-pryidylamide." should read -- γ-pyridylamide. --;
Column 19, lines 3-17, that part of formula XXXII reading

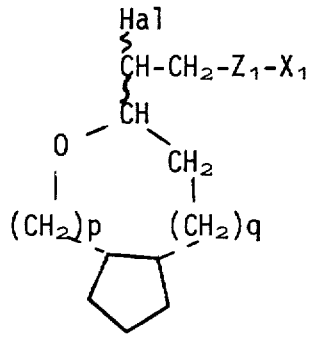   should read   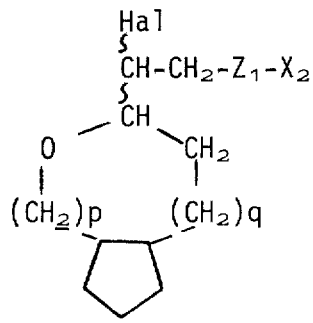

UNITED STATES PATENT OFFICE
CERTIFICATE OF CORRECTION

Patent No. 4,109,082  Dated 22 August 1978

Inventor(s) John C. Sih

It is certified that error appears in the above-identified patent and that said Letters Patent are hereby corrected as shown below:

Column 19, lines 20-35, that part of formula XXXIII reading

 should read 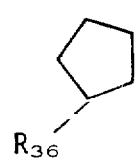

Column 20, that part of formula XLII reading

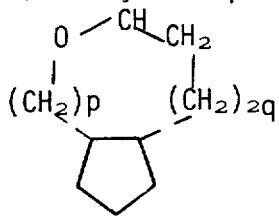 should read 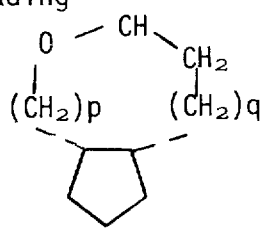

Column 21, that part of formula XLIV reading

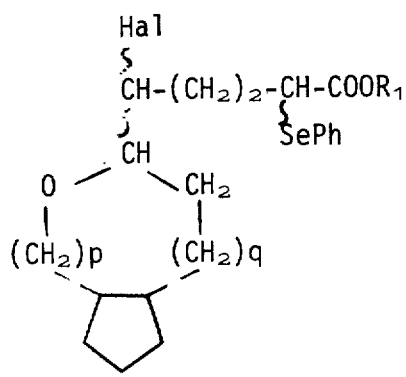 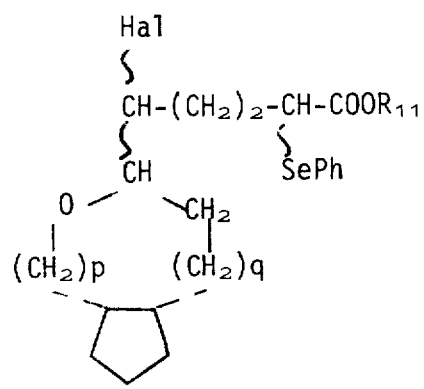

UNITED STATES PATENT OFFICE
CERTIFICATE OF CORRECTION

Patent No. 4,109,082     Dated 22 August 1978

Inventor(s) John C. Sih

It is certified that error appears in the above-identified patent and that said Letters Patent are hereby corrected as shown below:

Column 25, lines 2-12, that portion of formula L reading

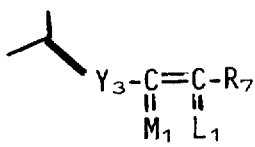    should read    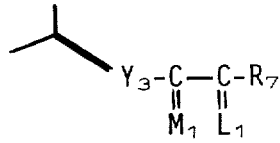

Column 25, lines 47-57, that portion of formula LXIII reading

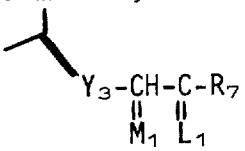    should read    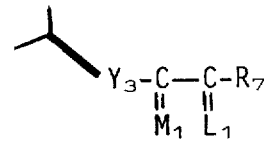

Column 28, lines 27-28, "($R_1$ is p-substituted phenyl," should read -- ($R_1$ is p-substituted phenyl), --;

Column 29, line 19, "PGP-type amino" should read -- PGF-type amino --

Column 35, line 58, "$6\alpha$-$PGI_1$-type compounds;" should read -- $6\beta$-$PGI_1$-type compounds; --;

Column 45, line 27, "$R_{21}$ and $R_{22}$ are" should read -- $R_{21}$ and $R_{23}$ are --.

Signed and Sealed this

Twenty-fourth Day of November 1981

[SEAL]

Attest:

GERALD J. MOSSINGHOFF

Attesting Officer     Commissioner of Patents and Trademarks